United States Patent
Peterkin et al.

(10) Patent No.: US 12,059,463 B2
(45) Date of Patent: Aug. 13, 2024

(54) PEPTIDE VACCINES AND PEMBROLIZUMAB FOR TREATING BREAST CANCER

(71) Applicant: ONCOPEP, INC., North Andover, MA (US)

(72) Inventors: Doris Peterkin, North Andover, MA (US); Marc A. Cohen, McLean, VA (US)

(73) Assignee: ONCOPEP, INC., Cambridge, MA (US)

( * ) Notice: Subject to any disclaimer, the term of this patent is extended or adjusted under 35 U.S.C. 154(b) by 407 days.

(21) Appl. No.: 16/758,682

(22) PCT Filed: Oct. 23, 2018

(86) PCT No.: PCT/US2018/057039
§ 371 (c)(1),
(2) Date: Apr. 23, 2020

(87) PCT Pub. No.: WO2019/083962
PCT Pub. Date: May 2, 2019

(65) Prior Publication Data
US 2020/0276304 A1  Sep. 3, 2020

Related U.S. Application Data

(60) Provisional application No. 62/576,404, filed on Oct. 24, 2017.

(51) Int. Cl.
*A61K 39/395* (2006.01)
*A61K 39/00* (2006.01)
*C07K 16/28* (2006.01)

(52) U.S. Cl.
CPC ... *A61K 39/3955* (2013.01); *A61K 39/001111* (2018.08); *A61K 39/001152* (2018.08); *A61K 2039/55522* (2013.01); *A61K 2039/55561* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 7,026,443 | B1 | 4/2006 | Sette et al. |
| 7,598,221 | B2 | 10/2009 | Scheinberg et al. |
| 9,096,681 | B2 | 8/2015 | Munshi et al. |
| 9,950,047 | B2 * | 4/2018 | Bae ............... A61K 39/001152 |

FOREIGN PATENT DOCUMENTS

| | | |
|---|---|---|
| CN | 105377288 A | 3/2016 |
| WO | 2002/22577 A2 | 3/2002 |
| WO | 2002/070003 A1 | 9/2002 |
| WO | 2014/071402 A1 | 5/2014 |

OTHER PUBLICATIONS

Isakoff et al (Journal of Clinical Oncology, May 30, 2017, 35, No. 15_supp. Abstract TPS1126).*
OncoPep press release, Feb. 22, 2017, 3 pages (Year: 2017).*
Bae et al (Clinical Cancer Research, 2012, 18:4850-4860) (Year: 2012).*
Wang et al (Blood, 2014, 124:4737) (Year: 2014).*
ClinicalTrials.gov NCT02826434, first post Jul. 7, 2016 (Year: 2016).*
ClinicalTrials.gov NCT02447003, first post May 14, 2015 (Year: 2015).*
Konstantinopoulos et al (Journal of Clinical Oncology, May 20, 2016; 34, No. 15_suppl; abstract TPS5599) (Year: 2016).*
Yuan et al (Oncoimmunology, 2017, 6:e1363138, published online Aug. 11, 2017) (Year: 2017).*
Chen et al (Nature, 2014, 508:103-107) (Year: 2014).*
ClinicalTrials.gov NCT02826434, first post Jul. 7, 2016.*
ClinicalTrials.gov NCT02447003, first post May 14, 2015.*
Konstantinopoulos et al (Journal of Clinical Oncology, May 20, 2016; 34, No. 15_suppl; abstract TPS5599).*
Yuan et al (Oncoimmunology, 2017, 6:e1363138, published online Aug. 11, 2017).*
Wang et al (Blood, 2014, 124:4737).*
Adams et al (Annals of Oncology, 2019, 30:405-411).*
Rugo et al (Clinical Cancer Research, 2018, 24:2804-2811).*
S.J.isakoff: "PVX-410 Vaccine Plus Pembrolizumab in HLA-A2+ Metastatic Triple Negative Breast Cancer", Clinical Trials Dec. 2, 2017 (Dec. 2, 2017), Retrieved from the Internet: URL:https://clinicaltrials.gov/ct2/history/NCT03362060?V_1= View#StudyPageTop [retrieved on Feb. 22, 2019].
Anonymous: "Adjuvant PVX-410 Vaccine and Durvalumab in Stage II/III Triple Negative Breast Cancer", Internet Citation, Jul. 11, 2016 (Jul. 11, 2016), pp. 1-8, XP002775296, Retrieved from the Internet: URL: https://clinicaltrials.gov/ct2/show/record/NCT02826434 [retrieved on Nov. 1, 2017].
Nanda et al., "Pembrolizumab in patients with advanced triple-negative breast cancer: Phase Ib Keynote-012 study" Journal of Clinical Oncology, 2016, vol. 34, No. 21, pp. 2460-2467.
Diana et al., "Triple-negative breast cancers: systematic review of the literature on molecular and clinical features with a focus on treatment with innovative drugs" Current Oncology Reports, 2018, vol. 18, No. 10, 11 pages.
International Search Report and Written Opinion for Application No. PCT/US2018/057039 mailed Apr. 8, 2019 (14 pages).
Mancebo et al., "Structure and expression of the *Drosophila melanogaster* gene for the U1 small nuclear ribonucleoprotein particle 70K protein" Molecular and Cellular Biology, 1990, vol. 10, No. 6, pp. 2492-2502.
Wentworth et al., "In Virto induction of primary, antigen-specific CTL from human peripheral blood mononuclear cells stimulated with synthetic peptides" Molecular Immunology, 1995, vol. 32, No. 9, pp. 603-612.

(Continued)

*Primary Examiner* — Laura B Goddard
(74) *Attorney, Agent, or Firm* — Lando & Anastasi, LLP

(57) ABSTRACT

The disclosure features, inter alia, combination therapies comprising pembrolizumab and one or more immunogenic XBP1-, CD138-, and CS1-derived peptides. The therapies herein can be used, e.g., for inducing an immune response in a subject having a cancer, and treating a cancer such as breast cancer, e.g., triple negative breast cancer.

12 Claims, No Drawings
Specification includes a Sequence Listing.

(56) References Cited

OTHER PUBLICATIONS

Celis et al., "Induction of anti-tumor cytotoxic T lymphocytes in normal humans using primary cultures and synthetic peptide epitopes" Proc. Natl. Acad. Sci. USA, 1994, vol. 91, pp. 2105-2109.

Wentworth et al., "Identification of A2-restricted hepatitis C virus-specific cytotoxic T lymphocyte epitopes from conserved regions of the viral genome" International Immunology, vol. 8, No. 5, pp. 651-659.

Altman et al., "Formation of functional peptide complexes of the class II major histocompatibility complex proteins from subunits produced in *Escherichia coli*" Proc. Natl. Acad. Sci. USA, 1993, vol. 90, pp. 10330-10334.

Kalergis et al., "Altered peptide ligand-mediated TCR antagonism can be modulated by a change in a single amino acid residue within the CDR3 b of an MHC class I-restricted TCR" J. Immunol., 2000, vol. 165, pp. 280-285.

WHO Drug Information, vol. 28, No. 3, 2014, 84 pages.

Holliger et al., "Enginerred antibody fragments and the rise of single domains" Nature Biotechnology, 2005, vol. 23, No. 9, pp. 1126-1136.

Clinical Trials "Standard of care chemotherapy plus pembrolizumab for breast cancer" Jul. 27, 2016, Retrieved from the Internet: URL: https://clinicaltrials.gov/ct2/show/NCT02734290?term=NCT02734290&rank=1.

Kawashima et al., "The multi-epitope approach for immunotherapy for cancer: identification of several CTL epitopes from various tumor-associated antigens expressed on solid epithelial tumors" Human Immunology, 1998, vol. 59, pp. 1-14.

Conlon et al., "Altered peptide ligands and MS treatment" Science, 2002, vol. 296, Issue 5574, 3 pages.

Wentworth et al., "Differences and similarities in the A2.1-restricted cytotoxic T cell repertoire in humans and human leukocyte antigen-transgenic mice" Eur. J. Immunol., 1996, vol. 26, pp. 97-101.

Altman et al., "Phenotypic analysis of antigen-specific T lymphocytes" Science, 1996, vol. 274, pp. 94-96.

Collins et al., "Altered peptide ligand design: altering immune responses to class I MHC/peptide complexes" Immunological Reviews, 1998, vol. 163, pp. 151-160.

Tsai et al., "Identification of subdominant CTL epitopes of the GP100 melanoma-associated tumor antigen by primary in vitro immunoization with peptide-pulsed dendritic cells" The Journal of Immunology, 1997, vol. 158, pp. 1796-1802.

Alexander et al., "Derivation of HLA-A11/Kb transgenic mice: functional CTL repertoire and recognition of human A11-restricted CTL epitopes" The Journal of Immunology, 1997, vol. 159, pp. 4753-4761.

Bea et al., "A multiepitope of XBP1, CD138 and CS1 peptides induces myeloma-specific cytotoxic T lymphocytes in T cells of smoldering myeloma patients" Leukemia, 2015, vol. 29(1), pp. 218-229.

"Pembrolizumab in Patients with Advanced Triple-Negative Breast Cancer: Phase Ib KEYNOTE-012 Study", Rita Nanda et al., Journal of Clinical Oncology, vol. 34, No. 21, pp. 2460-2469, published on Jul. 20, 2016.

* cited by examiner

SEQUENCE LISTING

```
<160> NUMBER OF SEQ ID NOS: 18

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Tyr Ile Ser Pro Trp Ile Leu Ala Val
1               5

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Tyr Leu Phe Pro Gln Leu Ile Ser Val
1               5

<210> SEQ ID NO 3
<211> LENGTH: 9
```

```
<212> TYPE: PRT
<213> ORGANISM: Homo sapiens

<400> SEQUENCE: 3

Gly Leu Val Gly Leu Ile Phe Ala Val
1               5

<210> SEQ ID NO 4
<211> LENGTH: 9
<212> TYPE: PRT
<213> ORGANISM: Homo sapiens

<400> SEQUENCE: 4

Ser Leu Phe Val Leu Gly Leu Phe Leu
1               5

<210> SEQ ID NO 5
<211> LENGTH: 261
<212> TYPE: PRT
<213> ORGANISM: Homo sapiens

<400> SEQUENCE: 5

Met Val Val Val Ala Ala Pro Asn Pro Ala Asp Gly Thr Pro Lys
1               5                   10                  15

Val Leu Leu Leu Ser Gly Gln Pro Ala Ser Ala Gly Ala Pro Ala
                20                  25                  30

Gly Gln Ala Leu Pro Leu Met Val Pro Ala Gln Arg Gly Ala Ser Pro
                35                  40                  45

Glu Ala Ala Ser Gly Gly Leu Pro Gln Ala Arg Lys Arg Gln Arg Leu
50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
                100                 105                 110

Leu Leu Glu Asn Gln Leu Leu Arg Glu Lys Thr His Gly Leu Val Val
                115                 120                 125

Glu Asn Gln Glu Leu Arg Gln Arg Leu Gly Met Asp Ala Leu Val Ala
                130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
                180                 185                 190

Val Leu Thr Leu Gln Ile Gln Ser Leu Ile Ser Cys Trp Ala Phe Trp
                195                 200                 205

Thr Thr Trp Thr Gln Ser Cys Ser Ser Asn Ala Leu Pro Gln Ser Leu
                210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
                260
```

-continued

```
<210> SEQ ID NO 6
<211> LENGTH: 376
<212> TYPE: PRT
<213> ORGANISM: Homo sapiens

<400> SEQUENCE: 6
```

Met Val Val Ala Ala Pro Asn Pro Ala Asp Gly Thr Pro Lys
1               5                   10                  15

Val Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
                35                  40                  45

Glu Ala Ala Ser Gly Gly Leu Pro Gln Ala Arg Lys Arg Gln Arg Leu
 50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Asn Gln Lys Leu
                100                 105                 110

Leu Leu Glu Asn Gln Leu Leu Arg Glu Lys Thr His Gly Leu Val Val
                115                 120                 125

Glu Asn Gln Glu Leu Arg Gln Arg Leu Gly Met Asp Ala Leu Val Ala
            130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Thr Pro Pro Glu
                165                 170                 175

His Leu Pro Met Asp Ser Gly Gly Ile Asp Ser Ser Asp Ser Glu Ser
                180                 185                 190

Asp Ile Leu Leu Gly Ile Leu Asp Asn Leu Asp Pro Val Met Phe Phe
            195                 200                 205

Lys Cys Pro Ser Pro Glu Pro Ala Ser Leu Glu Glu Leu Pro Glu Val
210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Lys Ile Glu Glu Ala Pro Leu Ser
                275                 280                 285

Pro Ser Glu Asn Asp His Pro Glu Phe Ile Val Ser Val Lys Glu Glu
290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
                355                 360                 365

Leu Phe Pro Gln Leu Ile Ser Val
    370                 375

<210> SEQ ID NO 7
<211> LENGTH: 310
<212> TYPE: PRT
<213> ORGANISM: Homo sapiens

<400> SEQUENCE: 7

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
            290                 295                 300

Gln Glu Glu Phe Tyr Ala
305                 310

<210> SEQ ID NO 8
<211> LENGTH: 335
<212> TYPE: PRT
<213> ORGANISM: Homo sapiens

<400> SEQUENCE: 8

Met Ala Gly Ser Pro Thr Cys Leu Thr Leu Ile Tyr Ile Leu Trp Gln
1               5                   10                  15

```
Leu Thr Gly Ser Ala Ala Ser Gly Pro Val Lys Glu Leu Val Gly Ser
                20                  25                  30

Val Gly Gly Ala Val Thr Phe Pro Leu Lys Ser Lys Val Lys Gln Val
            35                  40                  45

Asp Ser Ile Val Trp Thr Phe Asn Thr Thr Pro Leu Val Thr Ile Gln
50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
            130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
            195                 200                 205

Ile Leu Ala Arg Lys Leu Cys Glu Gly Ala Ala Asp Asp Pro Asp Ser
210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
            275                 280                 285

His Thr Asn Arg Thr Ile Leu Lys Glu Asp Pro Ala Asn Thr Val Tyr
290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 9
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
```

```
            35                  40                  45
Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 10
```

-continued

```
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val
        195                 200

<210> SEQ ID NO 11
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      KDEL motif"

<400> SEQUENCE: 11

Lys Asp Glu Leu
1

<210> SEQ ID NO 12
<211> LENGTH: 9
<212> TYPE: PRT
<213> ORGANISM: Homo sapiens

<400> SEQUENCE: 12

Arg Met Phe Pro Asn Ala Pro Tyr Leu
1               5

<210> SEQ ID NO 13
<211> LENGTH: 9
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Tyr Met Phe Pro Asn Ala Pro Tyr Leu
1               5

<210> SEQ ID NO 14
<211> LENGTH: 19
<212> TYPE: PRT
<213> ORGANISM: Homo sapiens

<400> SEQUENCE: 14

Arg Ser Asp Glu Leu Val Arg His His Asn Met His Gln Arg Asn Met
1               5                   10                  15

Thr Lys Leu

<210> SEQ ID NO 15
<211> LENGTH: 22
<212> TYPE: PRT
<213> ORGANISM: Homo sapiens

<400> SEQUENCE: 15

Pro Gly Cys Asn Lys Arg Tyr Phe Lys Leu Ser His Leu Gln Met His
1               5                   10                  15

Ser Arg Lys His Thr Gly
            20

<210> SEQ ID NO 16
<211> LENGTH: 19
<212> TYPE: PRT
<213> ORGANISM: Homo sapiens

<400> SEQUENCE: 16

Ser Gly Gln Ala Arg Met Phe Pro Asn Ala Pro Tyr Leu Pro Ser Cys
1               5                   10                  15

Leu Glu Ser

<210> SEQ ID NO 17
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Gly Gln Ala Tyr Met Phe Pro Asn Ala Pro Tyr Leu Pro Ser Cys
1               5                   10                  15

Leu Glu Ser

<210> SEQ ID NO 18
<211> LENGTH: 6
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 18

His His His His His His
1               5
```

PEPTIDE VACCINES AND PEMBROLIZUMAB FOR TREATING BREAST CANCER

This application is a U.S. national phase application and claims the benefit of priority under 35 U.S.C § 371 of International Application No. PCT/US2018/057039, filed on Oct. 23, 2018, which claims priority to U.S. Ser. No. 62/576,404 filed Oct. 24, 2017, the entire contents of which are incorporated herein by reference.

BACKGROUND

Several types of vaccines have been developed for the prevention of infectious diseases including attenuated microorganisms, recombinant proteins and DNA vaccines. Recently, research has been carried out on the development of vaccine immunotherapy to treat cancer patients.

SUMMARY

The present disclosure relates to combination therapies, e.g., one or more immunogenic peptides and pembrolizumab. In embodiments, the immunogenic peptides bind to MHC class 1 molecules such as HLA-A molecules. Peptides from X-Box Protein 1 (XBP1)-, CD138-, and CD2 Subset 1 (CS1) are immunogenic and are useful, e.g., to induce an immune response against various cancer cells.

It will be evident from the following description that the combination therapies herein can be used in a variety of applications such as methods for inducing an immune response in a patient, methods for activating a T cell (e.g., including effector memory T cells and/or central memory T cells), and methods for treating a cancer, e.g., a breast cancer, e.g., a triple negative breast cancer.

In some aspects, the present disclosure provides a method of treating a cancer, e.g., breast cancer, e.g., triple negative breast cancer, comprising administering to a subject:
  (i) pembrolizumab; and
  (ii) one or more of: a non-spliced XBP1 peptide described herein, a spliced XBP1 peptide described herein, a CD138 peptide described herein and a CS-1 peptide described herein;
  wherein the subject has, or is at risk of developing, a cancer, e.g., a breast cancer, e.g., a triple negative breast cancer.

In some aspects, the present disclosure provides pembrolizumab, in combination with: one or more of: a non-spliced XBP1 peptide described herein, a spliced XBP1 peptide described herein, a CD138 peptide described herein and a CS-1 peptide described herein;
for use in treating a cancer, e.g., a breast cancer, e.g., a triple negative breast cancer.

In some aspects, the present disclosure provides pembrolizumab, in combination with:
  (a) a non-spliced XBP1 peptide that is 35 amino acids or less in length and comprises the amino acid sequence of SEQ ID NO:1, e.g., a non-spliced XBP1 peptide that consists of the amino acid sequence of SEQ ID NO:1,
  (b) a spliced XBP1 peptide that is 35 amino acids or less in length and comprises the amino acid sequence of SEQ ID NO:2, e.g., a spliced XBP1 peptide that consists of the amino acid sequence of SEQ ID NO:2, and
  (c) a CD138 peptide that is 35 amino acids or less in length and comprises the amino acid sequence of SEQ ID NO:3, e.g., a CD138 peptide that consists of the amino acid sequence of SEQ ID NO:3;
  for use in treating a cancer, e.g., a breast cancer, e.g., a triple negative breast cancer.

In some aspects, the present disclosure provides pembrolizumab, in combination with:
  (a) a non-spliced XBP1 peptide that is 35 amino acids or less in length and comprises the amino acid sequence of SEQ ID NO:1, e.g., a non-spliced XBP1 peptide that consists of the amino acid sequence of SEQ ID NO:1,
  (b) a spliced XBP1 peptide that is 35 amino acids or less in length and comprises the amino acid sequence of SEQ ID NO:2, e.g., a spliced XBP1 peptide that consists of the amino acid sequence of SEQ ID NO:2,
  (c) a CD138 peptide that is 35 amino acids or less in length and comprises the amino acid sequence of SEQ ID NO:3, e.g., a CD138 peptide that consists of the amino acid sequence of SEQ ID NO:3, and
  (d) a CS-1 peptide that is 35 amino acids or less in length and comprises the amino acid sequence of SEQ ID NO:4, e.g., a CS-1 peptide that consists of the amino acid sequence of SEQ ID NO:4;
  for use in treating a cancer, e.g., a breast cancer, e.g., a triple negative breast cancer.

In some aspects, the present disclosure provides pembrolizumab, in combination with:
  (a) a non-spliced XBP1 peptide that consists of the amino acid sequence of SEQ ID NO:1,
  (b) a spliced XBP1 peptide that consists of the amino acid sequence of SEQ ID NO:2, and
  (c) a CD138 peptide that consists of the amino acid sequence of SEQ ID NO:3;
  for use in treating a cancer, e.g., a breast cancer, e.g., a triple negative breast cancer.

In some aspects, the present disclosure provides pembrolizumab, in combination with:
  (a) a non-spliced XBP1 peptide that consists of the amino acid sequence of SEQ ID NO:1,
  (b) a spliced XBP1 peptide that consists of the amino acid sequence of SEQ ID NO:2,
  (c) a CD138 peptide that consists of the amino acid sequence of SEQ ID NO:3, and
  (d) a CS-1 peptide that consists of the amino acid sequence of SEQ ID NO:4;
  for use in treating a cancer, e.g., a breast cancer, e.g., a triple negative breast cancer.

In some aspects, the present disclosure provides a method for inducing an immune response in a subject, the method comprising delivering to a subject:
  (i) pembrolizumab; and
  (ii) one or more of: a non-spliced XBP1 peptide described herein, a spliced XBP1 peptide described herein, a CD138 peptide described herein and a CS-1 peptide described herein.

In some aspects, the present disclosure provides pembrolizumab, in combination with:
  one or more of: a non-spliced XBP1 peptide described herein, a spliced XBP1 peptide described herein, a CD138 peptide described herein and a CS-1 peptide described herein;
  for use in inducing an immune response in a subject, e.g., a subject having breast cancer, e.g., a triple negative breast cancer.

In some aspects, the present disclosure provides pembrolizumab, in combination with:
  (a) a non-spliced XBP1 peptide that is 35 amino acids or less in length and comprises the amino acid sequence of SEQ ID NO:1, e.g., a non-spliced XBP1 peptide that consists of the amino acid sequence of SEQ ID NO:1, (b) a spliced XBP1 peptide that is 35 amino acids or less in length and comprises the amino acid sequence of SEQ ID NO:2, e.g., a spliced XBP1 peptide that consists of the amino acid sequence of SEQ ID NO:2, and (c) a CD138 peptide that is 35 amino acids or less in length and comprises the amino acid sequence of SEQ ID NO:3, e.g., a CD138 peptide that consists of the amino acid sequence of SEQ ID NO:3;

for use in inducing an immune response in a subject having breast cancer, e.g., a triple negative breast cancer.

In some aspects, the present disclosure provides pembrolizumab, in combination with:

(a) a non-spliced XBP1 peptide that is 35 amino acids or less in length and comprises the amino acid sequence of SEQ ID NO:1, e.g., a non-spliced XBP1 peptide that consists of the amino acid sequence of SEQ ID NO:1, (b) a spliced XBP1 peptide that is 35 amino acids or less in length and comprises the amino acid sequence of SEQ ID NO:2, e.g., a spliced XBP1 peptide that consists of the amino acid sequence of SEQ ID NO:2, and (c) a CD138 peptide that is 35 amino acids or less in length and comprises the amino acid sequence of SEQ ID NO:3, e.g., a CD138 peptide that consists of the amino acid sequence of SEQ ID NO:3, and (d) a CS-1 peptide that is 35 amino acids or less in length and comprises the amino acid sequence of SEQ ID NO:4, e.g., a CS-1 peptide that consists of the amino acid sequence of SEQ ID NO:4;

for use in inducing an immune response in a subject having breast cancer, e.g., a triple negative breast cancer.

In some aspects, the present disclosure provides pembrolizumab, in combination with:

(a) a non-spliced XBP1 peptide that consists of the amino acid sequence of SEQ ID NO:1, (b) a spliced XBP1 peptide that consists of the amino acid sequence of SEQ ID NO:2, and (c) a CD138 peptide that consists of the amino acid sequence of SEQ ID NO:3;

for use in inducing an immune response in a subject having breast cancer, e.g., a triple negative breast cancer.

In some aspects, the present disclosure provides pembrolizumab, in combination with:

(a) a non-spliced XBP1 peptide that consists of the amino acid sequence of SEQ ID NO:1, (b) a spliced XBP1 peptide that consists of the amino acid sequence of SEQ ID NO:2, (c) a CD138 peptide that consists of the amino acid sequence of SEQ ID NO:3, and (d) a CS-1 peptide that consists of the amino acid sequence of SEQ ID NO:4;

for use in inducing an immune response in a subject having breast cancer, e.g., a triple negative breast cancer.

In some aspects, the present disclosure provides a method of treating a breast cancer, e.g., a triple negative breast cancer, comprising administering to a subject:

(i) pembrolizumab; and (ii):

(a) a non-spliced XBP1 peptide that is 35 amino acids or less in length and comprises the amino acid sequence of SEQ ID NO:1, e.g., a non-spliced XBP1 peptide that consists of the amino acid sequence of SEQ ID NO:1, (b) a spliced XBP1 peptide that is 35 amino acids or less in length and comprises the amino acid sequence of SEQ ID NO:2, e.g., a spliced XBP1 peptide that consists of the amino acid sequence of SEQ ID NO:2, and (c) a CD138 peptide that is 35 amino acids or less in length and comprises the amino acid sequence of SEQ ID NO:3, e.g., a CD138 peptide that consists of the amino acid sequence of SEQ ID NO:3.

In some aspects, the present disclosure provides a method of treating a breast cancer, e.g., a triple negative breast cancer, comprising administering to a subject:

(i) pembrolizumab; and (ii):

(a) a non-spliced XBP1 peptide that consists of the amino acid sequence of SEQ ID NO:1, (b) a spliced XBP1 peptide that consists of the amino acid sequence of SEQ ID NO:2, and (c) a CD138 peptide that consists of the amino acid sequence of SEQ ID NO:3.

Any of the aspects above can also involve one or more of the embodiments below:

In some embodiments, the non-spliced XBP1 peptide is 35 amino acids or less in length and comprises the amino acid sequence of SEQ ID NO:1. In some embodiments, the spliced XBP1 peptide is 35 amino acids or less in length and comprises the amino acid sequence of SEQ ID NO:2. In some embodiments, the CD138 peptide is 35 amino acids or less in length and comprises the amino acid sequence of SEQ ID NO:3. In some embodiments, the CS-1 peptide is 35 amino acids or less in length and comprises the amino acid sequence of SEQ ID NO:4.

In some embodiments, the non-spliced XBP1 peptide consists of the amino acid sequence of SEQ ID NO:1. In some embodiments, the spliced XBP1 peptide consists of the amino acid sequence of SEQ ID NO:2. In some embodiments, the CD138 peptide consists of the amino acid sequence of SEQ ID NO:3. In some embodiments, the CS-1 peptide consists of the amino acid sequence of SEQ ID NO:4.

In some embodiments, the method comprises administering, or the composition for use comprises: (a) a non-spliced XBP1 peptide described herein, (b) a spliced XBP1 peptide described herein, and (c) a CD138 peptide described herein. In some embodiments, the method comprises administering, or the composition for use comprises: (a) a non-spliced XBP1 peptide that is 35 amino acids or less in length and comprises the amino acid sequence of SEQ ID NO:1, (b) a spliced XBP1 peptide that is 35 amino acids or less in length and comprises the amino acid sequence of SEQ ID NO:2, and (c) a CD138 peptide that is 35 amino acids or less in length and comprises the amino acid sequence of SEQ ID NO:3. In some embodiments, the method comprises administering, or the composition for use comprises: (a) a non-spliced XBP1 peptide that consists of the amino acid sequence of SEQ ID NO:1, (b) a spliced XBP1 peptide that consists of the amino acid sequence of SEQ ID NO:2, and (c) a CD138 peptide that consists of the amino acid sequence of SEQ ID NO:3. In some embodiments, the method comprises administering, or the composition for use further comprises: (d) a CS-1 peptide described herein. In some embodiments, the method comprises administering, or the composition for use further comprises: (d) a CS-1 peptide that is 35 amino acids or less in length and comprises the amino acid sequence of SEQ ID NO:4. In some embodiments, the method comprises administering, or the composition for use further comprises: (d) a CS-1 peptide that consists of the amino acid sequence of SEQ ID NO:4.

In some embodiments, the method comprises administering, or the composition for use comprises, one or more immune stimulating agents. In some embodiments, the immune stimulating agent is selected from an adjuvant comprising carboxymethylcellulose, polyinosinic-polycytidylic acid, and poly-L-lysine double-stranded RNA (e.g., poly IC-LC, e.g., hiltonol); an adjuvant comprising a water-and-oil emulsion (e.g., montanide); and an adjuvant comprising a protein (e.g., a cytokine, GCSF, or GM-CSF). In some embodiments, the method comprises administering, or the composition for use further comprises an additional treatment, e.g., one or more chemotherapeutic agents, one or more forms of ionizing radiation, one or more immunotherapy agents (e.g., a cancer vaccine, an immune checkpoint inhibitor), one or more immune checkpoint inhibitors, e.g., an antibody which inhibits an immune checkpoint molecule (e.g., an anti-CTLA4 antibody, e.g., ipilimumab or tremelimumab, a PD-1 antibody, or a PDL-1 antibody), or an adjuvant, e.g., a small molecule adjuvant (e.g., thalidomide or a thalidomide derivative, e.g., lenalidomide). In some embodiments, the method comprises administering, or the composition for use further comprises lenalidomide. In some embodiments, the method comprises administering, or the composition for use further comprises poly IC-LC.

In some embodiments, the cancer is breast cancer. In some embodiments, the breast cancer is triple negative breast cancer. In some embodiments, the subject has, or is at risk of developing, or is suspected of having, breast cancer, e.g., triple negative breast cancer. In some embodiments, the subject has, or is identified as having, one or more cancer cells that express XBP1, CD138, or CS1, or any combination thereof. In some embodiments, the method further comprises, after delivering the composition to the subject, determining if an immune response occurred in the subject. In some embodiments, the subject is a human. In some embodiments, the subject is in remission from breast cancer, e.g., triple negative breast cancer.

In some embodiments, the pembrolizumab of (i) and the peptides of (ii) are administered separately or together. In some embodiments, (i) is administered before, concurrently with, or after (ii). In some embodiments, (i) and (ii) are formulated for use separately or together. In some embodiments, (i) is formulated for administration before, concurrently with, or after (ii).

In some embodiments, the pembrolizumab is administered at a dose of 200 mg. In some embodiments, the pembrolizumab is administered once every three weeks.

In some embodiments, the one or more peptides are administered at a dose of 0.8 mg total peptide, e.g., at 0.2 mg of the non-spliced XBP1 peptide, 0.2 mg of the spliced XBP1 peptide, 0.2 mg of the CD138 peptide, and 0.2 mg of the CS-1 peptide. In some embodiments, the one or more peptides are administered at a dose of 0.4-1.2 mg total peptide, e.g., at 0.1-0.3 mg of the non-spliced XBP1 peptide, 0.1-0.3 mg of the spliced XBP1 peptide, 0.1-0.3 mg of the CD138 peptide, and 0.1-0.3 mg of the CS-1 peptide. In some embodiments, the one or more peptides are administered at a dose of 0.8-1.2 mg total peptide, e.g., at 0.2-0.3 mg of the non-spliced XBP1 peptide, 0.2-0.3 mg of the spliced XBP1 peptide, 0.2-0.3 mg of the CD138 peptide, and 0.2-0.3 mg of the CS-1 peptide. In some embodiments, the one or more peptides are administered at a dose of 0.4-1.6 mg total peptide, e.g., at 0.1-0.4 mg of the non-spliced XBP1 peptide, 0.1-0.4 mg of the spliced XBP1 peptide, 0.1-0.4 mg of the CD138 peptide, and 0.1-0.4 mg of the CS-1 peptide. In some embodiments, the one or more peptides are administered at a dose of 0.8-1.6 mg total peptide, e.g., at 0.2-0.4 mg of the non-spliced XBP1 peptide, 0.2-0.4 mg of the spliced XBP1 peptide, 0.2-0.4 mg of the CD138 peptide, and 0.2-0.4 mg of the CS-1 peptide.

In some embodiments, the one or more peptides are administered at a dose of 0.6 mg total peptide, e.g., at 0.2 mg of the non-spliced XBP1 peptide, 0.2 mg of the spliced XBP1 peptide, and 0.2 mg of the CD138 peptide. In some embodiments, the one or more peptides are administered at a dose of 0.3-0.9 mg total peptide, e.g., at 0.1-0.3 mg of the non-spliced XBP1 peptide, 0.1-0.3 mg of the spliced XBP1 peptide, and 0.1-0.3 mg of the CD138 peptide. In some embodiments, the one or more peptides are administered at a dose of 0.6-0.9 mg total peptide, e.g., at 0.2-0.3 mg of the non-spliced XBP1 peptide, 0.2-0.3 mg of the spliced XBP1 peptide, and 0.2-0.3 mg of the CD138 peptide. In some embodiments, the one or more peptides are administered at a dose of 0.3-1.2 mg total peptide, e.g., at 0.1-0.4 mg of the non-spliced XBP1 peptide, 0.1-0.4 mg of the spliced XBP1 peptide, and 0.1-0.4 mg of the CD138 peptide. In some embodiments, the one or more peptides are administered at a dose of 0.6-1.2 mg total peptide, e.g., at 0.2-0.4 mg of the non-spliced XBP1 peptide, 0.2-0.4 mg of the spliced XBP1 peptide, and 0.2-0.4 mg of the CD138 peptide.

In embodiments, the peptides are administered as a first dose and one or more additional doses. In embodiments, the one or more peptides are administered every two weeks, e.g., for at least 1, 2, 3, 4, 5, 6, 8, 10, or 12 weeks. In embodiments, the one or more peptides are administered once weekly. In embodiments, the one or more peptides are administered every 1, 2, 3, or 4 weeks, e.g., for at least 1, 2, 3, 4, 5, 6, 8, 10, or 12 weeks. In embodiments, the one or more peptides are administered two or more times over the course of 12, 18, 24, 30, or 36 months, e.g., over the course of 18-24 months. In embodiments, an additional dose is administered at about 9-12, 12-18, 18-24, 24-30, or 30-36 months after the first dose. In embodiments, the one or more peptides are administered to the subject at least 2, 3, 4, 5, 6, 7, 8, 9, or 10 times, e.g., at least 4 or 6 times.

The present disclosure also provides, in certain aspects, a composition comprising:
  (i) pembrolizumab; and
  (ii) one or more of: a non-spliced XBP1 peptide described herein, a spliced XBP1 peptide described herein, a CD138 peptide described herein and a CS-1 peptide described herein.

The present disclosure also provides, in certain aspects, a kit comprising:
  (i) pembrolizumab; and
  (ii) one or more of: a non-spliced XBP1 peptide described herein, a spliced XBP1 peptide described herein, a CD138 peptide described herein and a CS-1 peptide described herein.

In embodiments, (i) and (ii) are admixed, and in embodiments, (i) and (ii) are separate, e.g., in separate containers.

In embodiments, the peptides herein include one or more of XBP1 peptides, CD138 peptides and CS-1 peptides, that have affinity for multiple MHC molecules, e.g., HLA-A molecules such as HLA-A2, elevated stability within the peptide binding cleft of multiple MHC molecules, e.g., HLA-A2, and the ability, when expressed on the surface of cell (e.g., a cancer cell) in the context of an MHC molecule, e.g., HLA-A2, to induce the activation and proliferation of T cells including, e.g., effector memory T cells and/or central memory T cells).

It will be evident from the description herein that the combination therapies herein can be used in a variety of applications such as methods for inducing an immune response in a patient having a cancer, methods for activating a T cell (e.g., effector memory T cells and/or central memory T cells) in a patient having a cancer, methods for producing an antibody in a patient having a cancer, and methods for treating cancer e.g., breast cancer, e.g., triple negative breast cancer. In some embodiments, induction of an immune response comprises inducing a subject to produce an antibody against one or more of the peptides.

In some embodiments, the combination therapy comprises an isolated peptide comprising an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-4. The peptide can bind to a major histocompatibility complex (MHC) molecule such as an MHC class I or class II molecule. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:1-4, or an amino acid sequence that is at least 70%, 75%, 80%, 85%, 90%, 95%, 96%, 97%, 98% or 99% identical to an amino acid sequence of any of SEQ ID NOS:1-4. In one embodiment, the peptide is 9, 10, 11, 12, 13, 14, 15, 16, 17, 18, 19, 20, up to 25, 30 or 35 amino acids in length and comprises an amino acid sequence of any one of SEQ ID NOS:1-4. In one embodiment, the peptide is 9, 10, 11, 12, 13, 14, 15, 16, 17, 18, 19, 20, up to 25, 30 or 35 amino acids in length and the peptide comprises an amino acid sequence with three, two, or one substitution(s) of an amino acid sequence of any one of SEQ ID NOS:1-4. The substitutions can be conservative or non-conservative.

In one embodiment, the peptide consists of an amino acid sequence that is at least 66 (e.g., at least 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99) % identical to any one of SEQ ID NOS:1-4. In one embodiment, the peptide consists of any of amino acid sequences of SEQ ID NOS:1-4 with three, two or one substitution. In one embodiment, the peptide consists of an amino acid sequence of any one of SEQ ID NOS:1-4.

In some embodiments, any of the isolated peptides described herein can, in association with a major histocompatibility complex (MHC) molecule, be recognized by an antigen specific T cell receptor on a T cell.

In some embodiments, the combination therapy comprises a fusion protein that comprises a first amino acid sequence consisting of a peptide described herein, e.g., a non-spliced XBP1 peptide described herein, a spliced XBP1 peptide described herein, a CD138 peptide described herein and/or a CS-1 peptide described herein; and a second amino acid sequence that is heterologous to the first amino acid sequence.

In some embodiments, the second amino acid sequence can comprise, or be, a targeting polypeptide, an immune stimulatory molecule, an immunoglobulin or antigen-binding fragment thereof, an Fc receptor-binding region of an immunoglobulin molecule, or a carrier polypeptide. The targeting polypeptide can be, e.g., one that targets the isolated peptide to an antigen presenting cell (e.g., a dendritic cell, a macrophage, a monocyte, or a B cell). The immune stimulatory molecule can be, e.g., a cytokine or a T helper epitope. The immunoglobulin can be, e.g., a single chain Fv immunoglobulin fragment or an entire immunoglobulin molecule. The carrier polypeptide can comprise, or be, a KLH (keyhole limpet hemocyanin) polypeptide, or an albumin polypeptide.

In some embodiments, any of the isolated peptides described herein can contain a linker sequence. The linker sequence can directly or indirectly connect a first amino acid sequence to a second amino acid sequence. The linker sequence can comprise, or consist of, one or more amino acids, e.g., at least one, two, three, four, five, six, seven, eight, nine or ten amino acids. In one embodiment, the linker can comprise, or consist of, at least one (e.g., one, two, three, four, five, six, seven, eight, nine, or 10 or more) protease cleavage site.

In some embodiments, the second amino acid sequence can be amino terminal or carboxy terminal to the first amino acid sequence.

In some embodiments, any of the isolated peptides or fusion proteins described herein can be detectably labeled. The detectable label can be selected from the group consisting of luminescent labels, fluorescent labels, radioactive labels, and enzymatic labels.

In some embodiments, the combination therapy comprises (e.g., the pharmaceutical composition herein comprises, or the method of treatment herein comprises administering) at least two peptides, e.g., 2, 3, 4 or more of the peptides described herein.

In one embodiment, the combination therapy comprises at least two peptides. For example, the combination therapy comprises a non-spliced XBP1 peptide and a spliced XBP1 peptide; the combination therapy comprises a non-spliced XBP1 peptide and a CD138 peptide; the combination therapy comprises a non-spliced XBP1 peptide and a CS-1 peptide; the combination therapy comprises a spliced XBP1 peptide and a CD138 peptide; the combination therapy comprises a spliced XBP1 peptide, and a CS-1 peptide; the combination therapy comprises a CD138 peptide and a CS-1 peptide.

In one embodiment, the combination therapy comprises at least three peptides. For example, the combination therapy comprises a non-spliced XBP1 peptide, a spliced XBP1 peptide, and a CD138 peptide; the combination therapy comprises a non-spliced XBP1 peptide, a spliced XBP1 peptide, and a CS-1 peptide; the combination therapy comprises a non-spliced XBP1 peptide, a CD138 peptide, and a CS-1 peptide; the combination therapy comprises a spliced XBP1 peptide, a CD138 peptide, and a CS-1 peptide. In one embodiment, the combination therapy comprises at least three peptides, e.g., a non-spliced XBP1 peptide, a spliced XBP1 peptide, and a CD138 peptide.

In one embodiment, the combination therapy comprises four peptides, e.g., the combination therapy comprises a non-spliced XBP1 peptide, a spliced XBP1 peptide, a CD138 peptide, and a CS-1 peptide.

In one embodiment, the combination therapy comprises a non-spliced XBP1 peptide that is 9, 10, 11, 12, 13, 14, 15, 16, 17, 18, 19, 20, up to 25, 30 or 35 amino acids in length and comprises an amino acid sequence of SEQ ID NO:1. In one embodiment, the combination therapy comprises a spliced XBP1 peptide that is 9, 10, 11, 12, 13, 14, 15, 16, 17, 18, 19, 20, up to 25, 30 or 35 amino acids in length and comprises an amino acid sequence of SEQ ID NO:2. In one embodiment, the combination therapy comprises a CD138 peptide that is 9, 10, 11, 12, 13, 14, 15, 16, 17, 18, 19, 20, up to 25, 30 or 35 amino acids in length and comprises an amino acid sequence of SEQ ID NO:3. In one embodiment, the combination therapy comprises a CS-1 peptide that is 9, 10, 11, 12, 13, 14, 15, 16, 17, 18, 19, 20, up to 25, 30 or 35 amino acids in length and comprises an amino acid sequence of SEQ ID NO:4.

In one embodiment, the combination therapy comprises four peptides and the four peptides are: a peptide that comprises (e.g., consists of) the amino acid sequence of SEQ ID NO:1, a peptide that comprises (e.g., consists of) the amino acid sequence of SEQ ID NO:2, a peptide that comprises (e.g., consists of) the amino acid sequence of SEQ ID NO:3, and a peptide that comprises (e.g., consists of) the amino acid sequence of SEQ ID NO:4.

The combination therapy can also include, e.g., one or more additional agents, e.g., one or more therapeutic agents, diagnostic agents, or prophylactic agents, or immune stimulating or modulating agents. Immune stimulating agents include, but are not limited to, e.g., a T helper epitope, an altered peptide ligand, an adjuvant, or any other immune stimulating agent described herein. The T helper epitope can be, e.g., a PADRE sequence or a universal Tetanus Toxoid T helper (TT Th) epitope. The adjuvant can be selected from the group consisting of Freund's complete adjuvant, Freund's incomplete adjuvant, alum, a ligand for a Toll receptor, saponin (e.g., QS21), RIBI, cholera toxin (CT), E. coli heat labile toxin (LT), mutant CT (MCT), mutant E. coli heat labile toxin (MLT), an adjuvant comprising carboxymethylcellulose, polyinosinic-polycytidylic acid, and poly-L-lysine double-stranded RNA (e.g., poly IC-LC, e.g., hiltonol), an adjuvant comprising a water-and-oil emulsion (e.g., montanide), and an adjuvant comprising a protein (e.g., cytokines, complements, GCSF, or GM-CSF). In one embodiment, the immune stimulating agent is an adjuvant comprising carboxymethylcellulose, polyinosinic-polycytidylic acid, and poly-L-lysine double-stranded RNA, e.g., poly IC-LC, e.g., hiltonol. In one embodiment the adjuvant is a water-and-oil emulsion, e.g., montanide. In one embodiment, the adjuvant is a protein, e.g., a cytokine, a complement, GCSF, or GM-CSF. In one embodiment, the additional agent can be a protein, e.g., an antibody. In one embodiment, the additional agent is an immune checkpoint inhibitor. For example, an antibody which inhibits an immune checkpoint molecule can be an anti-CTLA4 antibody, e.g., ipilimumab or tremelimumab, or an anti-PD-1 antibody, or anti-PDL-1 antibody. In one embodiment, the additional agent can be a small molecule adjuvant, e.g., thalidomide or a thalidomide derivative, e.g., lenalidomide.

The combination therapy may also include an immunogenic peptide other than one disclosed above, e.g., an immunogenic peptide from WT1 or a derivative thereof. Exemplary WT1 peptides are described in U.S. Pat. No. 7,598,221, the contents of which is incorporated herein by reference. In one embodiment, the combination therapy comprises one or more immunogenic peptide from WT1 or a derivative thereof, e.g., selected from one or more of: a WT1 class 1 epitope; a peptide comprising (or consisting of) RMFPNAPYL (WT1 126-134); a peptide comprising (or consisting of) YMFPNAPYL; a peptide comprising (or consisting of) RSDELVRHHNMHQRNMTKL (WT1 427-445); a peptide comprising (or consisting of) PGCNKRYFKLSHLQMHSRKHTG (WT1 331-352); a peptide comprising (or consisting of) SGQARMFPNAPYLPSCLES (WT1 122-140); and a peptide comprising (or consisting of) SGQAYMFPNAPYLPSCLES. Other immunogenic peptides include, but are not limited to, an immunogenic peptide from MUC1, an immunogenic peptide from gp100, an immunogenic peptide from TRP-2, an immunogenic peptide from MAGI, an immunogenic peptide from NY-ESO1, an immunogenic peptide from HER-2; and an immunogenic peptide from AIM2.

In one embodiment, the composition described herein is used to treat a subject having or at risk of having a cancer, e.g., a breast cancer described herein, e.g., triple negative breast cancer.

In some embodiments, the kits described herein comprise instructions for administering the peptide to a subject having a cancer, e.g., a breast cancer, e.g., triple negative breast cancer.

In some embodiments, the kits can also include, e.g., one or more pharmaceutically acceptable carriers, one or more immune stimulating or modulating agents, or one or more therapeutic agents, diagnostic agents, or prophylactic agents. In one embodiment, the immune stimulating agent is an immune stimulating agent described herein. The one or more immune stimulating agents can be selected from the group consisting of a T helper epitope, an altered peptide ligand, and an adjuvant. In one embodiment, the immune stimulating agent is an adjuvant comprising carboxymethylcellulose, polyinosinic-polycytidylic acid, and poly-L-lysine double-stranded RNA (e.g., poly IC-LC, e.g., hiltonol); an adjuvant comprising a water-and-oil emulsion (e.g., montanide); an adjuvant comprising a protein (e.g., a cytokine, a complement, GCSF, or GM-CSF). In one embodiment, the additional agent can be a protein, e.g., an antibody. In one embodiment, the additional agent is an immune checkpoint inhibitor. For example, an antibody which inhibits an immune checkpoint molecule can be an anti-CTLA4 antibody, e.g., ipilimumab or tremelimumab, or an anti-PD-1 antibody, or anti-PDL-1 antibody. In one embodiment, the additional agent can be a small molecule adjuvant, e.g., thalidomide or a thalidomide derivative, e.g., lenalidomide. In one embodiment, the kit further comprises instructions for administering an immune stimulating agent and/or immune modulating agent in combination with a peptide or peptides described herein or a composition described herein.

In one embodiment, the kit further comprises an additional immunogenic peptide, e.g., an immunogenic peptide from WT1 or a derivative thereof, e.g., an immunogenic WT1 peptide described herein. Other immunogenic peptides include, but are not limited to, an immunogenic peptide from MUC1, an immunogenic peptide from gp100, an immunogenic peptide from TRP-2, an immunogenic peptide from MAGI, an immunogenic peptide from NY-ESO1, an immunogenic peptide from HER-2; and an immunogenic peptide from AIM2. In one embodiment, the kit further comprises instructions for administering an additional immunogenic peptide, e g., a WT1 peptide, in combination with a peptide or peptides described herein or a composition described herein.

The methods described herein for inducing an immune response in a subject can include the step of delivering, e.g., administering, to a subject one or more of any of the isolated peptides described herein and/or a composition described herein. In one embodiment, the subject is administered at least two, e.g., 2, 3 or 4, of the peptides from SEQ ID NOS: 1-4. For example, the subject can be administered two or more of a non-spliced XBP1 peptide, a spliced XBP1 peptide, a CD138 peptide, a CS-1 peptide, and combinations thereof.

The method can also include the step of, after delivering the one or more peptides or composition to the subject, determining if an immune response occurred in the subject. The one or more peptides can be delivered to the subject as a pharmaceutical composition, e.g., a pharmaceutical composition described herein. The subject can be, e.g., a mammal (e.g., a human) or any other subject described herein. The subject can have, be suspected of having, at risk of developing, or in remission from a cancer, e.g., a breast cancer, e.g., triple negative breast cancer.

In some embodiments, the method can include determining whether the cancer cell (or cells) expresses one or more of XBP1, CD138, or CS-1.

In some embodiments, the method can further include administering to the subject one or more additional treatment, e.g., a chemotherapeutic agent, ionizing radiation, surgery or one or more additional immunotherapy agents. The one or more forms of ionizing radiation can be, e.g., gamma-irradiation, X-irradiation, or beta-irradiation. The one or more chemotherapeutic agents can be a chemotherapeutic agent described herein, e.g., a chemotherapeutic agent selected from the group consisting of a platinum based agent, a taxane, a topoisomerase inhibitor, an antimetabolite, an alkylating agent, a protease inhibitor, an HDAC inhibitor, and a vinca alkaloid. Exemplary chemotherapeutic agents include, but are not limited to: cisplatin, carboplatin procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, taxol, transplatinum, 5-flurouracil, vincristin, vinblastin, methotrexate, and an analog of any of the aforementioned. The method can also include administering to the subject one or more immune stimulating agents, e.g., one or more immune stimulating agents described herein.

In one embodiment, the method further comprises administering an additional immunogenic peptide, e.g., an immunogenic peptide from WT1 or a derivative thereof, e.g., an immunogenic WT1 peptide described herein, in combination with the one or more peptides described herein. Other immunogenic peptides include, but are not limited to, an immunogenic peptide from MUC1, an immunogenic peptide from gp100, an immunogenic peptide from TRP-2, an immunogenic peptide from MAGI, an immunogenic peptide from NY-ESO1, an immunogenic peptide from HER-2; and an immunogenic peptide from AIM2.

In some embodiments, the delivering comprises administering to the subject the one or more peptides described herein (e.g., one or more peptides comprising any of SEQ ID NOS:1-4). In some embodiments, the delivering comprises administering to the subject one or more nucleic acids, each of which comprises a nucleotide sequence encoding the one or more peptides, the nucleotide sequence being operably-linked to an expression control sequence. The nucleic acid can be in a recombinant cell transfected with the nucleic acid and expressing the one or more peptides. The recombinant cell can be a transfected cell, or the progeny of a transfected cell, made by transfecting a cell obtained from the subject. The recombinant cell can be an antigen presenting cell such as, but not limited to, a dendritic cell, a macrophage, a monocyte, or a B cell.

In some embodiments of any of the above-described methods, the delivering includes: contacting the one or more peptides to a cell; and after contacting the one or more peptides to the cell, delivering the cell to the subject. The cell can be, e.g., an antigen presenting cell such as any of those described herein. The cell can be, e.g., a cell, or the progeny of a cell, obtained from the subject. In some embodiments, the cell can be a cell, or the progeny of a cell, obtained from another subject of the same species as the subject. The other subject can express at least one MHC molecule in common with the subject. The at least one MHC molecule can be, e.g., an MHC class I molecule such as an HLA-A2 molecule.

In one embodiment, the method further comprises administering an additional agent to the subject, e.g., administering a chemotherapeutic agent and/or an immune stimulating agent and/or an immune modulating agent. In one embodiment, the additional agent is an immune stimulating agent, e.g., an immune stimulating agent described herein. In one embodiment, the immune stimulating agent is an adjuvant comprising carboxymethylcellulose, polyinosinic-polycytidylic acid, and poly-L-lysine double-stranded RNA (e.g., poly IC-LC, e.g., hiltonol); an adjuvant comprising a water-and-oil emulsion (e.g., montanide); an adjuvant comprising a protein (e.g., a cytokine, a complement, GCSF, or GM-CSF). In one embodiment, the additional agent can be a protein, e.g., an antibody. In one embodiment, the additional agent is an immune checkpoint inhibitor. For example, an antibody which inhibits an immune checkpoint molecule can be an anti-CTLA4 antibody, e.g., ipilimumab or tremelimumab, or an anti-PD-1 antibody, or anti-PDL-1 antibody. In one embodiment, the additional agent can be a small molecule adjuvant, e.g., thalidomide or a thalidomide derivative, e.g., lenalidomide. In one embodiment, the method comprises administering an additional immunogenic peptide, e.g., an immunogenic peptide from WT1 or a derivative thereof, e.g., a WT1 peptide described herein, in combination with the one or more of the peptides. Other immunogenic peptides include, but are not limited to, an immunogenic peptide from MUC1, an immunogenic peptide from gp100, an immunogenic peptide from TRP-2, an immunogenic peptide from MAGI, an immunogenic peptide from NY-ESO1, an immunogenic peptide from HER-2; and an immunogenic peptide from AIM2.

In one embodiment, the method further comprises administering one or more additional dose of a peptide or composition described herein. In one embodiment, the subject is administered one or more additional dose about 14 days after the previous dose, e.g., the subject is administered 2, 3, 4, 5, 6, 7, 8, 9 or 10 doses of a peptide or composition described herein, every other week. In one embodiment, the subject is administered one or more additional dose about 7 days after the previous dose, e.g., the subject is administered 2, 3, 4, 5, 6, 7, 8, 9 or 10 doses of a peptide or composition described herein, once weekly.

In some embodiments, the methods herein include a step of selecting a treatment for a mammal in need thereof. The method can include the steps of: determining if one or more cancer cells in a mammal express XBP1; and if one or more of the cancer cells express XBP1, selecting as a therapeutic agent for the mammal one or more of the peptides described herein, fusion proteins comprising such peptides, or compositions described herein. The method can also include the step of, after determining that one or more of the cells of the cancer express XBP1, delivering to the subject one or more of the peptides described herein, fusion proteins comprising such peptides, or compositions described herein.

In some embodiments of any of the above methods, the subject or mammal can be one who has received a therapy for a cancer, e.g., a breast cancer, e.g., triple negative breast cancer, and was non-responsive to the therapy, e.g., combination therapies described herein may be a second-line, third line or fourth-line treatment.

Unless otherwise defined, all technical and scientific terms used herein have the same meaning as commonly understood by one of ordinary skill in the art to which this invention pertains. In case of conflict, the present document, including definitions, will control. Various suitable methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., methods for inducing an immune response in a subject, will be apparent from the following description and from the claims.

DETAILED DESCRIPTION

Peptides

The combination therapies herein comprise one or more immunogenic XBP1-, CD138-, and CS-1-derived peptides (and pharmaceutical compositions thereof). The therapies herein can be used to, e.g., induce an immune response (e.g., stimulate a CTL response), or stimulate the production of an antibody, in a subject having a cancer.

A detailed description of the peptides as well as exemplary methods for making and using the peptides are set forth below.

The disclosure features combination therapies comprising one or more isolated peptides comprising an amino acid sequence that has sufficient identity with or is identical to any one of SEQ ID NOS:1-4 as depicted in Table 1.

TABLE 1

Examples of XBP1, CD138, and CS1 peptides

| Protein of Origin | Amino Acid Position | Amino Acid Sequence | SEQ ID NO: |
|---|---|---|---|
| non-spliced XBP1 | 185-193 | YISPWILAV | 1 |
| spliced XBP1 | 368-376 | YLFPQLISV | 2 |
| CD138 | 260-268 | GLVGLIFAV | 3 |
| CS1 | 239-247 | SLFVLGLFL | 4 |

Bolded residues indicate amino acid changes from the corresponding wild-type amino acid sequence.

In some embodiments, the isolated peptide is at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprises an amino acid sequence that has at least 70%, 75%, 80%, 85%, 90%, 95%, 96%, 97%, 98%, 99% identity or is identical to an amino acid sequence of SEQ ID NOS:1-4. Other suitable peptides can be at least 9, 10, 11, 12, 13, 14, 15, 16, 17, 18, 19, 20, 25, 30 or 35 amino acids in length (e.g., between 9 and 35 amino acids in length, e.g., 9-30, 9-25, 9-20, 9-15 amino acids in length) and comprise an amino acid sequence of SEQ ID NOS:1-4, or an amino acid sequence with one, two, three or four substitutions of the amino acid sequence of SEQ ID NOs:1-4 The substitution can be a conservative or nonconservative substitution.

"Non-spliced XBP1" peptides include a peptide of SEQ ID NO: 1 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the non-spliced form of human XBP1 protein having 261 amino acids and the following sequence: MVVVAAAPN-PADGTPKVLLLSGQPASAAGAPAGQALPLMVPAQR-GASPEAASGGLPQ ARKRQRLTHLSPEEKA-LRRKLKNRVAAQTARDRKKARMSELEQQVVDLE-EENQKLLLE NQLLREKTHGLVVENQELRQRLGM-DALVAEEEAEAKGNEVRPVAGSAESAALRLRAPL QQVQAQLSPLQNISPWILAVLTLQIQSLIS-CWAFWTTWTQSCSSNALPQSLPAWRSSQRS TQKDPVPYQPPFLCQWGRHQPSWKPLMN (SEQ ID NO:5; Genbank Accession No. NP_005071), and peptides having no more than one, two, three, four, five substitutions (e.g., conservative substitutions) of the amino acids derived from the amino acid sequence of SEQ ID NO:5. The non-spliced XBP1 amino acid positions referred to in Table 1 are based on SEQ ID NO: 5.

"Spliced XBP1" peptides include a peptide of SEQ ID NO: 2 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 31, 32, 33, 34 or 35) consecutive amino acids from the spliced form of human XBP1 (XBP1 spliced) protein having 376 amino acids and the following sequence: MVVVAAAPN-PADGTPKVLLLSGQPASAAGAPAGQALPLMVPAQR-GASPEAASGGLPQ ARKRQRLTHLSPEEKA-LRRKLKNRVAAQTARDRKKARMSELEQQVVDL-EEENQKLLLE NQLLREKTHGLVVENQELRQRLGM-DALVAEEEAEAKGNEVRPVAGSAESAAGAGPVV TPPEHLPMDSGGIDSSDSESDILLGILD-NLDPVMFFKCPSPEPASLEELPEVYPEGPSSLPA SLSLSVGTSSAKLEAINELIRFDHIYTKPLVLEIPSE-TESQANVVVKIEEAPLSPSENDHPEF IVSVKEEPVED-DLVPELGISNLLSSSHCPKPSSCLLDAYSDCGYGGSL-SPFSDMSSLLGVN HSWEDTFANELFPQLISV (SEQ ID NO: 6; Genbank Accession No. NP_001073007), and peptides having no more than one, two, three, four, five substitutions (e.g., conservative substitutions) of the amino acids derived from the amino acid sequence of SEQ ID NO:6. The spliced XBP1 amino acid positions referred to in Table 1 are based on SEQ ID NO: 6.

"CD138" peptides include a peptide of SEQ ID NO: 3 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CD138 protein having 310 amino acids and the following sequence: MRRAALWLWLCALALSLQPALPQI-VATNLPPEDQDGSGDDSDNFSGSGAGALQDITLS QQTPSTWKDTQLLTAIPTSPEPTGLEATAAS TSTL-PAGEGPKEGEAVVLPEVEPGLTARE QEATPR-PRETTQLPTTHQASTTTATTAQEPAT-SHPHRDMQPGHHETSTPAGPSQADLHTP HTEDGGPSATERAAEDGASSQLPAAEGSGEQDFT-FETSGENTAVVAVEPDRRNQSPVDQ GATGASQGLL-DRKEVLGGVIAGGLVGLIFAVCLVGFMLYRMKKK-DEGSYSLEEPKQAN GGAYQKPTKQEEFYA (SEQ ID NO:7; Genbank Accession No. NP_002988) and peptides having no more than one, two, three, four, five substitutions (e.g., conservative substitutions) of the amino acids derived from the amino acid sequence of SEQ ID NO:7. The CD138 amino acid positions referred to in Table 1 are based on SEQ ID NO: 7.

"CS-1" peptides include a peptide of SEQ ID NO: 4 and refer to a peptide having an amino acid sequence of at least 5 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35) consecutive amino acids from the human CS-1 protein having 335 amino acids and the following sequence: MAGSPTCLTLIYILWQLTGSAASGPVKELVGSVG-GAVTFPLKSKVKQVDSIVWTFNTTP LVTIQPEGGTIIVTQNRNRERVDFPDGGYSLKLSKLK-KNDSGIYYVGIYSSSLQQPSTQEY VLHVYEHL-SKPKVTMGLQSNKNGTCVTNLTCCMEHGEED-VIYTWKALGQAANESHNG SILPISWRWGESDMTFICVARNPVSRNFSSPILARKL-CEGAADDPDSSMVLLCLLLVPLLL SLFVLGLFLW-FLKRERQEEYIEEKKRVDICRETPNICPHSGENTEYD-TIPHTNRTILKEDPA NTVYSTVEIPKKMENPHSLLTMPDTPRLFAYENVI (SEQ ID NO:8; Genbank Accession No. NP_067004) and peptides having no more than one, two, three, four, five substitutions (e.g., conservative substitutions) of the amino acids derived from the amino acid sequence of SEQ ID NO:8. The CS-1 amino acid positions referred to in Table 1 are based on SEQ ID NO: 8.

Peptides Generally

The peptides described herein are often referred to using the residue number of the N and C terminal amino acids of the peptides (e.g., $XBP1_{118-126}$) as the relevant sequences occur in the wild-type, full length, mature human proteins having SEQ ID NOS: 5-8. These peptides will frequently have identical sequences to the corresponding segments of the wild-type, full-length, mature proteins having SEQ ID NOS: 5-8. It is understood, however, that the terms "non-spliced XBP1 peptides" (e.g., nonspliced XBP1 peptides having amino acid positions: 118-136, 185-193, 186-194, 190-198, 193-200, or 111-119), "spliced XBP1 peptides" (e.g., spliced XBP1 peptides having amino acid positions: 197-205, 194-202, 224-232, 368-376), "CD138 peptides" (e.g., CD138 peptides having amino acid positions: 256-264, 265-273, 260-268, 5-13, or 7-15), and "CS1 peptides" (e.g., CS-1 peptides have amino acid positions 236-245, 240-248, 239-247, 232-240, or 9-17) can be peptide fragments of the XBP1 nonspliced peptide, the XBP1 spliced peptide, the CD138, or CS-1 polypeptide (respectively) of a species other than human. As will be appreciated by those skilled in the art, the numbers of the N and C terminal amino acids of peptide fragments of such non-human polypeptides are not necessarily the same as those in the corresponding peptide fragments of human polypeptides. Moreover, the lengths and/or amino acids of peptide fragments of non-human polypeptides will not necessarily be the same as those in the corresponding peptide fragments of human polypeptides. Those of skill in the art will know how to establish the N and C terminal amino acids, the lengths, and amino acid sequences of peptides derived from non-human nonspliced XBP1, spliced XBP1, CD138, and CS-1 polypeptides. One useful method for doing this is sequence alignment and, in particular, maximum homology sequence alignment.

Percent identity between two peptide sequences (e.g., a peptide of SEQ ID NOS: 1-4) and another amino acid sequence that may be at least 66% identical to the peptide) can be determined using a variety of algorithms and computer programs including, but not limited to, Clustal W (The European Bioinformatics Institute (EMBL-EBI), BLAST-Protein (National Center for Biotechnology Information (NCBI), United States National Institutes of Health), and PSAlign (University of Texas A&M; Sze et al. (2006) Journal of Computational Biology 13:309-319).

Some of the peptides described herein are heteroclitic. As used herein, "heteroclitic" (e.g., a heteroclitic peptide) refers to a form of a peptide in which one or more amino acids have been modified from a wild-type or original sequence in order to produce a peptide that is more immunogenic than the corresponding wild-type peptide. For example, in the exemplary heteroclitic peptides of SEQ ID NO: 1 and SEQ ID NO: 2, the bolded amino acids indicate the amino acids that are modified from the wild-type sequence of XBP1.

Also disclosed herein are variants of the human and non-human peptides described above. Variants of the human and non-human peptides described herein can include forms of the peptides having: (i) not more than 4 (e.g., 3, 2, or 1) amino acid substitutions (e.g., conservative or non-conservative substitutions); (ii) terminal or internal deletions; or (iii) terminal or internal additions, all of which are elaborated on below.

The disclosure also features combination therapies comprising peptides comprising, consisting of, or consisting essentially of, an amino acid sequence of any of SEQ ID NOs: 1-4, but with not more than four (e.g., not more than three, not more than two, or not more than 1) substitutions. The substitutions can be, e.g., conservative or non-conservative (as described above).

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

In some embodiments, one or more (e.g., one, two, three, four, or all five) of positions three, four, five, six, seven, and eight of any of the peptides are not substituted. In some embodiments, one or more of positions three, four, five, six, seven, and eight of any of the peptides are identical to the amino acids of the peptides in Table 1.

Also featured are fusion proteins comprising: a first amino acid sequence of a peptide described herein (e.g., a non-spliced XBP1 peptide described herein, a spliced XBP1 peptide described herein, a CD138 peptide described herein and/or a CS-1 peptide described herein); and a second amino acid sequence that is heterologous to the first amino acid sequence.

The second, heterologous amino acid sequence(s) of the peptide generally do not (and are selected such that do not) adversely affect the generation in the cell of an immunogenic peptide of any of SEQ ID NOs: 1-4. The cellular machinery is expected to remove any additional sequences in the peptide to yield an immunogenic peptide of any of SEQ ID NOs: 1-4, which peptide is presented by a class I or class II MHC molecule to stimulate an immune response against XBP1-, CD138-, or CS1-expressing cancer cells.

An amino acid sequence that is "heterologous" to a first amino acid sequence, or the term "heterologous amino acid sequence," is any amino acid sequence other than the amino acid sequence(s) flanking the first amino acid sequence as it occurs in nature. For example, two or more (e.g., two, three, four, five, six, seven, eight, nine, 10, 11, 12, 13, 14, 15, 16, 17, 18, 19, or 20 or more) and/or less than 20 (e.g., 19, 18, 17, 16, 15, 14, 13, 12, 11, 10, nine, eight, seven, six, five, four, three, two, or one) carboxy- and/or amino-terminal amino acid(s) immediately flanking GLVGLIFAV (SEQ ID NO:3) in a human CD138 are not considered to be heterologous to SEQ ID NO:3. It is understood that a fusion protein containing a first amino acid sequence that is less than 100% identical to, or contains from one to four conservative substitutions in, an amino acid sequence of any of SEQ ID NOs: 1-4, may not occur in nature at all.

In some embodiments, the second amino acid sequence can be a single amino acid. It is understood that an amino acid that is "heterologous" to a first amino acid sequence, or the term "heterologous amino acid," is any amino acid other than the amino acid(s) flanking the first amino acid sequence as it occurs in nature. For example, the two amino acid(s) immediately flanking GLVGLIFAV (SEQ ID NO:3) in a human CD138 are not considered to be heterologous to SEQ ID NO:3.

A heterologous sequence can be, for example, a sequence used for purification of the recombinant protein (e.g., FLAG, polyhistidine (e.g., hexahistidine), hemagglutinin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the fusion protein can contain a signal sequence from another protein such as a KDEL (SEQ ID NO:11) sequence or any other described herein. In some embodiments, the fusion protein can contain all or part of an immunoglobulin molecule (e.g., all or part of an immunoglobulin heavy chain constant region; see below). In some embodiments, the fusion protein can contain a therapeutic or immune-stimulating polypeptide (e.g., a T helper epitope (e.g., a PADRE epitope or a Tetanus Toxoid universal T helper cell epitope) or all or part of a cytokine or chemokine) and/or a carrier (e.g., KLH) useful, e.g., in eliciting an immune response (e.g., for antibody generation). In some embodiments, the fusion protein can contain one or more linkers, e.g., a linker comprising a peptide sequence (see below). The fusion protein can also contain a targeting polypeptide. Heterologous sequences can be of varying length and in some cases can be longer sequences than the first amino acid sequences to which the heterologous amino acid sequences are attached. It is understood that a fusion protein containing a first amino acid sequence and a second amino acid sequence that is heterologous to the first does not correspond in sequence to a naturally occurring protein.

Targeting polypeptides, as used herein, are polypeptides that target the moiety (or moieties) they are attached to (e.g., the first amino acid sequence) to specific tissues (e.g., to a lymph node) or cells (e.g., to an antigen presenting cell or other immune cell), or where in vitro, specific isolated molecules or molecular complexes. Targeting polypeptides can be, e.g., an antibody (immunoglobulin) or antigen binding fragment thereof or a ligand for a cell surface receptor. An antibody (or antigen-binding fragment thereof) can be, e.g., a monoclonal antibody, a polyclonal antibody, a humanized antibody, a fully human antibody, a single chain antibody, a chimeric antibody, or an Fab fragment, an $F(ab')_2$ fragment, an Fab' fragment, an Fv fragment, or an scFv fragment of an antibody. Antibody fragments that include, or are, Fc regions (with or without antigen-binding regions) can also be used to target the reagents to Fc receptor-expressing cells (e.g., antigen presenting cells such as interdigitating dendritic cells, macrophages, monocytes, or B cells). A ligand for a cell surface receptor can be, e.g., a chemokine, a cytokine (e.g., interleukins 1, 2, 3, 4, 5, 6, 7, 8, 9, 10, 11, 12, 13, 14, 15, or 16), or a death receptor ligand (e.g., FasL or TNFα).

In some embodiments, the heterologous sequence can be, e.g., a "transportation sequence" that aids in the delivery of the peptide to the cell or to a specific compartment of a cell (e.g., the endoplasmic reticulum or Golgi apparatus). Transportation sequences can include, e.g., membrane translocating sequence, a transportan sequence, an antennapedia sequence, a cyclic integrin-binding peptide, and a Tat-mediated peptide, or modified versions thereof.

A linker, e.g., a linker peptide, can, directly or indirectly, connect the first amino acid sequence to one or more heterologous amino acid sequences. For example, a linker can connect the first amino acid sequence to a second amino acid sequence. A linker peptide can be, or contain, e.g., stretches of amino acids where at least four to six amino acids are glycine. (See, e.g., Mancebo et al. (1990) Mol. Cell. Biol. 10:2492-2502). A linker peptide can also be, or contain, six or more (e.g., seven, eight, nine, 10, 11, or 12 or more) histidine residues. The linker peptide can be, or contain, at least one (e.g., one, two, three, four, five, six, seven, or eight or more) protease cleavage site(s). The protease sites can be, e.g., a trypsin, a chymotrypsin, or a factor Xa cleavage site. Such protease sites can be useful, e.g., to separate a first amino acid sequence from a heterologous sequence. For example, after expression and purification of a fusion protein containing a first amino acid sequence joined to a polyhistidine sequence (in this case used for purification) by a trypsin protease cleavage site, the polyhistidine sequence can be removed from first amino acid sequence by contacting the fusion protein with trypsin.

The first amino acid sequence and the second amino acid sequence can be associated with each other in a variety of ways. As used herein, "associated with" in the context of an interaction between two or more atoms or molecular units, includes any covalent or non-covalent bonding, or physical admixture, of two or more atoms or molecular units (e.g., a first amino acid sequence and a second amino acid sequence). The chemical nature of covalent bonds (two atoms sharing one or more pairs of valence electrons) are known in the art and include, e.g., disulfide bonds or peptide bonds. A non-covalent bond is a chemical bond between atoms or molecules that does not involve the sharing of pairs of valence electrons. For example, non-covalent interactions include, e.g., hydrophobic interactions, hydrogen-bonding interactions, ionic bonding, Van der Waals bonding, or dipole-dipole interactions. Examples of such non-covalent interactions include antibody-antigen complexing or binding pair interactions (interactions of a first and second member of a binding pair such as the interaction between streptavidin and biotin). It is understood that the term "associated with" (e.g., in the context of a first amino acid sequence and a second amino acid sequence) is thus coextensive with the term "comprising."

In some embodiments, the first amino acid sequence and second amino acid sequence can be encoded by (and expressed as fusion protein from) a single nucleic acid sequence. In some instances, the first amino acid sequence and second amino acid sequence can be encoded by two or more (e.g., three, four, five, or six or more) different nucleic acid sequences. For example, the first amino acid sequence can be encoded by a first nucleic acid sequence and the second amino acid sequence can be encoded by a second nucleic acid sequence.

When expressed or produced separately, a first amino acid sequence and a second amino acid sequence can be cross-linked together using any of a number of known chemical cross linkers. Examples of such chemical cross-linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable chemical cross-linker, 4-succinimidyloxycarbonyl-α-methyl-α(2-pyridyldithio)toluene (SMPT), forms such a linkage between the two amino acid sequences utilizing a terminal lysine on one of the amino acid sequences and a terminal cysteine on the other. Heterobifunctional reagents which cross-link by a different coupling moiety on each amino acid sequence. In this way, the resulting "dimers" will be heterodimers (peptides containing the first and second amino acid sequences) rather than either homodimers (e.g., two first amino acid sequences or two second amino acid sequences) or a mixture of homodimers and heterodimers. Thus, the coupling moiety on a first amino acid sequence could be a cysteine residue and on the other a lysine residue. Other useful cross-linkers include, without limitation, chemicals that link two amino groups (e.g., N-5-Azido-2-nitrobenzoyloxysuccinimide), two sulfhydryl groups (e.g., 1,4-Bis-maleimidobutane) an amino group and a sulfhydryl group (e.g., m-Maleimidobenzoyl-N-hydroxysuccinimide ester), an amino group and a carboxyl group (e.g., 4-[p-Azidosalicylamido]butylamine), and an amino group and a guanadium group that is present in the side chain of arginine (e.g., p-Azidophenyl glyoxal monohydrate).

The coupling moieties will, in some embodiments, be at the termini (C or N) of each amino acid sequence. They can be, as indicated above, a cysteine residue on each amino acid sequence, or a cysteine on one and a lysine on the other. Where they are two cysteine residues, cross-linking can be effected by, for example, exposing amino acid sequences to oxidizing conditions.

A fusion protein can contain a first amino acid sequence and a second amino acid sequence or the fusion protein can contain more than one (e.g., two, three, four, five, six, seven, or eight or more) additional heterologous amino acid sequences. The additional heterologous amino acid sequences can flank, or be joined to, the amino terminus and/or the carboxy-terminus of the first amino acid sequence.

Where more than two amino acid sequences are to be joined, at least one of the amino acid sequences can have more than one cross-linking moiety. For example, a first amino acid sequence can have a cross-linking moiety at the amino-terminus and carboxy-terminus. Such multimers can be constructed "sequentially." Thus, each amino acid sequence is joined to the next such that the terminal amino acid sequences in the chain only have one residue involved in an inter-domain (or inter-agent) bond while the "internal" amino acid sequence(s) each have two moieties involved in inter-domain bonds. Alternatively, one amino acid sequence (such as the first amino acid sequence) could be linked to multiple (e.g., 2, 3, 4, or 5) other amino acid sequences.

A combination therapy described herein can include a first component and a second component, wherein the first component is a peptide described herein. The second component can be, e.g., a heterologous amino acid sequence (as described above), any other antigenic peptide (e.g., a peptide other than those described herein, a detectable label (see below), a therapeutic agent, or a prophylactic agent (see below). For example, a peptide composition can contain an amino acid sequence consisting of, or consisting essentially of, any of SEQ ID NOs: 1-4 and a detectable label such as a radionuclide.

It is understood that in some embodiments, a peptide described herein can have at the amino-terminal end and/or carboxy-terminal end up to 200 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200) amino acids that are heterologous.

The peptides described herein can bind to a major histocompatibility complex (MHC) molecule (e.g., an MHC class I molecule or an MHC class II molecule). The "Major Histocompatibility Complex" or "MHC" is a cluster of genes that plays a role in control of the cellular interactions responsible for physiologic immune responses. In humans, the MHC is known as the HLA complex (see, e.g., Paul et al., FUNDAMENTAL IMMUNOLOGY, 3$^{rd}$ Edition, Raven Press, New York, (1993) and Stites, et al., IMMUNOLOGY, 8$^{th}$ Edition, Lange Publishing, Los Altos, Calif. (1994)).

An "HLA supertype or family," as used herein, refers to sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like molecules (where xx denotes a particular HLA type), are synonyms. Types of HLA class I molecules include, e.g., HLA-A1, HLA-A2, HLA-A3, HLA-A24, HLA-B7, HLA-B27, HLA-B44, HLA-B58, or HLA-B62. Such HLA molecules are described in detail in U.S. Pat. No. 7,026,443, the entire disclosure of which is incorporated by reference in its entirety.

A peptide can bind to an MHC molecule with high affinity or intermediate affinity. As used herein, "high affinity" binding of a peptide to an HLA class I molecule is defined as a binding with a dissociation constant ($K_D$) of less than 50 (e.g., 45, 40, 35, 30, 25, 20, 15, 10, 5, 1, 0.5, 0.1, or less than 0.05) nM. "Intermediate affinity" is a binding of a peptide to an HLA class I molecule with a $K_D$ of between about 50 nM and about 500 nM (e.g., 55, 60, 65, 70, 75, 80, 85, 90, 95, 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nM). "High affinity" binding of a peptide to HLA class II molecules is defined as binding with a $K_D$ of less than 100 (e.g., 95, 90, 85, 80, 75, 70, 65, 60, 55, 50, 45, 40, 35, 30, 25, 20, 15, 10, 5, 1, 0.5, 0.1, or less than 0.05) nM. "Intermediate affinity" of a peptide for an HLA class II molecule is binding with a $K_D$ of between about 100 and about 1000 nM (e.g., 100, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nM). Methods for determining the binding affinity of a peptide and an MHC molecule are described in, e.g., U.S. Pat. No. 7,026,443.

The peptides described herein can also be, in association with an MHC molecule, recognized by an antigen specific T cell receptor on a T cell. A variety of suitable methods can be used to determine whether a peptide, in association with an MHC molecule, is recognized by a T cell receptor on a T cell. For example, peripheral blood lymphocytes (PBL) from normal subjects can be cultured with a test peptide in the presence of antigen presenting cells in vitro over a period of several weeks. T cells specific for the peptide become activated during this time and can be detected using, e.g., proliferation assays (carboxyfluoroscein succinimidyl ester (CFSE) assays or $^3$H-thymidine assays), limiting dilution assays, cytotoxicity assays (e.g., calcein-release assays), or cytokine-(e.g., IFNγ), lymphokine-, or $^{51}$Cr-release assays (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998, the disclosures of each of which are incorporated by reference in their entirety). A suitable in vivo method involves immunizing HLA transgenic mice, wherein peptides in adjuvant are administered subcutaneously to HLA transgenic mice and several weeks following immunization, splenocytes are removed and cultured in vitro in the presence of test peptide for approximately one week and peptide-specific T cells are detected using, e.g., a $^{51}$Cr-release assay (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997, the disclosures of each of which are incorporated by reference in their entirety).

Additionally, direct quantification of antigen-specific T cells can be performed by staining T cells with detectably-labeled MHC complexes such as any of the MHC molecule multimer compositions described in International Application WO2014/071402, or HLA-I tetramers (e.g., as described in Altman, J. D. et al., Proc. Natl. Acad. Sci. USA 90:10330, 1993 and Altman, J. D. et al., Science 274:94, 1996, the disclosures of each of which are incorporated by reference in their entirety).

In some embodiments, the peptides can be modified (e.g., amino acids of the peptides can be substituted) in order to modulate (e.g., increase or decrease) one of more properties of the peptides. For example, one or more (e.g., two, three, or four) amino acids of one of the peptides depicted in Table 1 can be substituted in order to increase the affinity of the peptide for an MHC molecule. In some embodiments, an amino acid of one of the peptides described herein (e.g., a T cell Receptor contacting amino acid residue of the peptide) can be modified in order to enhance a binding interaction between a T cell receptor and the peptide (in the context of an MHC molecule). Such modified peptides are often referred to as "altered peptide ligands." (See, e.g., Kalergis et al. (2000) J Immunol. 165(1):280; Conlon et al. (2002) Science 1801; and International Publication No. WO02070003, the disclosure of each of which is incorporated by reference in their entirety).

Suitable methods for modifying the peptides as well as determining the effect of the modification are described in, e.g., International Application WO2014/071402 and Collins et al. (Immunlogical Reviews (1998) 163:151-160, the disclosure of each of which is incorporated by reference in its entirety).

Suitable methods for producing the peptides herein, and nucleic acids encoding the peptides, are described in, e.g., the sections entitled "Nucleic Acids and Methods for Producing the Peptides" and "Additional Processing of the Peptides" in International Application WO2014/071402, which application is herein incorporated by reference in its entirety.

The peptides (and fusion proteins) described herein can, but need not, be isolated. The term "isolated," as applied to any of the peptides (or fusion proteins) described herein, refers to a peptide, a fragment thereof, (or for compositions, a macromolecular complex), that has been separated or purified from components (e.g., proteins or other naturally-occurring biological or organic molecules) which naturally accompany it. It is understood that recombinant molecules (e.g., recombinant peptides) will always be "isolated." Typically, a peptide (or fragment or macromolecular complex) is isolated when it constitutes at least 60%, by weight, of the total molecules of the same type in a preparation, e.g., 60% of the total molecules of the same type in a sample. For example, a peptide described herein is considered isolated when it constitutes at least 60%, by weight, of the total protein in a preparation or sample. In some embodiments, a molecule in the preparation consists of at least 75%, at least 90%, or at least 99%, by weight, of the total molecules of the same type in a preparation. A peptide can also be "isolated" when it is present in a mixture with other isolated peptides, e.g., a mixture of equal mass amounts of two, three, or four different peptides.

In some embodiments, the isolated peptides, fusion proteins, peptide-coding sequences, fusion protein-coding sequences or vectors can be frozen, lyophilized, or immobilized and stored under appropriate conditions, which allow the molecules to retain activity (e.g., the ability of a peptide to bind to an MHC molecule such as an MHC class I molecule or the ability of a vector to support expression of a peptide in a cell).

Additional Processing of the Peptides

Following the expression or synthesis of any of the peptides (or fusion proteins) described herein, the peptides (or fusion proteins) can be further processed. The further processing can include chemical or enzymatic modifications to peptides (or fusion protein) or, in cases where the peptides (or fusion proteins) are modified, the processing can include enzymatic or chemical alterations of existing modifications, or both. The additional processing of the peptides can include the addition (covalent or non-covalent joining) of a heterologous amino acid sequence such as, but not limited to, any of the heterologous amino acid sequences described above. Enzymatic treatment can involve contacting a peptide with, e.g., one or more proteases, phosphatases, or kinases under conditions that allow the peptide to be modified. Enzymatic treatment can involve contacting a peptide with one or more enzymes (e.g., an oligosaccharyltransferase or a mannosidase) capable of glycosylating, or modifying the glycosylation of, the peptide.

The processing can include the addition of, e.g., a detectable label to a peptide. For example, a peptide can be detectably labeled with an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine, fluorescein, dansyl chloride, allophycocyanin (APC), or phycoerythrin), a luminescent material (e.g., a lanthanide or chelate thereof), a bioluminescent material (e.g., luciferase, luciferin, or aequorin), or a radio-nuclide (e.g., $^3$H, $^{32}$P, $^{33}$P, $^{125}$I, or $^{35}$S).

The processing can also involve the coupling of the peptide (or fusion protein) to a polymer (e.g., a polyalkylene glycol moiety such as a polyethylene glycol moiety). In some embodiments, the polymer is coupled to the peptide at a site on the peptide that is an N terminus.

In some embodiments, a peptide can contain one or more internal amino acid insertions that provide an internal polymer conjugation site to which a polymer can be conjugated. Pembrolizumab The combination therapies herein include pembrolizumab. Pembrolizumab is a monoclonal anti-PD-1 antibody molecule having the light chain and heavy chain sequence set out below.

The International Nonproprietary Names for Pharmaceutical Substances (INN) (WHO Drug Information, Vol. 28, No. 3, 2014) (incorporated by reference in its entirety, including the section entitled "pembrolizumab" on p. 407) provides the pembrolizumab heavy and light chain sequences as:

```
Pembrolizumab Heavy chain sequence:
                                                    (SEQ ID NO: 9)
QVQLVQSGVE VKKPGASVKV SCKASGYTFT NYYMYWVRQA PGQGLEWMGG  50

INPSNGGTNF NEKFKNRVTL TTDSSTTTAY MELKSLQFDD TAVYYCARRD 100

YRFDMGFDYW GQGTTVTVSS ASTKGPSVFP LAPCSRSTSE STAALGCLVK 150

DYFPEPVTVS WNSGALTSGV HTFPAVLQSS GLYSLSSVVT VPSSSLGTKT 200

YTCNVDHKPS NTKVDKRVES KYGPPCPPCP APEFLGGPSV FLFPPKPKDT 250

LMISRTPEVT CVVVDVSQED PEVQFNWYVD GVEVHNAKTK PREEQFNSTY 300

RVVSVLTVLH QDWLNGKEYK CKVSNKGLPS SIEKTISKAK GQPREPQVYT 350

LPPSQEEMTK NQVSLTCLVK GFYPSDIAVE WESNGQPENN YKTTPPVLDS 400

DGSFFLYSRL TVDKSRWQEG NVFSCSVMHE ALHNHYTQKS LSLSLGK   447

Pembrolizumab Light chain sequence:
                                                    (SEQ ID NO: 10)
EIVLTQSPAT LSLSPGERAT LSCRASKGVS TSGYSYLHWY QQKPGQAPRL  50

LIYLASYLES GVPARFSGSG SGTDFTLTIS SLEPEDFAVY YCQHSRDLPL 100

TFGGGTKVEI KRTVAAPSVF IFPPSDEQLK SGTASVVCLL NNFYPREAKV 150

QWKVDNALQS GNSQESVTEQ DSKDSTYSLS STLTLSKADY EKHKVYACEV 200
```

Pembrolizumab can be formulated for parenteral administration, e.g., intravenous administration.

In embodiments, pembrolizumab is administered at 200 mg every 3 weeks. In embodiments, pembrolizumab is administered every 3, 4, 5, 6, 7, 8, 9, 10, 11, or 12 weeks. In embodiments, pembrolizumab is administered intravenously. In embodiments, pembrolizumab is administered intravenously over the course of 30 minutes. In embodiments, pembrolizumab is administered at 2 mg/kg body weight every 3 weeks.

In embodiments, the combination therapies herein comprise administering pembrolizumab and a peptide composition described herein. In embodiments, the combination therapies herein comprise administering an antibody molecule related to pembrolizumab (e.g., in place of pembrolizumab in any of the methods herein). In embodiments, the antibody molecule comprises a heavy chain sequence having at least 70%, 80%, 85%, 90%, 95%, 96%, 97%, 98%, or 99% identity to SEQ ID NO: 9. In embodiments, the antibody molecule comprises a light chain sequence having at least 70%, 80%, 85%, 90%, 95%, 96%, 97%, 98%, or 99% identity to SEQ ID NO: 10. In embodiments, the antibody molecule comprises a VH region having at least 70%, 80%, 85%, 90%, 95%, 96%, 97%, 98%, or 99% identity to the VH region from SEQ ID NO: 9, or having the CH region from SEQ ID NO: 9. In embodiments, the antibody molecule comprises a VL region having at least 70%, 80%, 85%, 90%, 95%, 96%, 97%, 98%, or 99% identity to the VL region from SEQ ID NO: 10, or having the VL region from SEQ ID NO: 10. In embodiments, the antibody molecule comprises a HC CDR1, HC CDR2, and HC CDR3 from SEQ ID NO: 9, wherein the CDRs are defined according to Kabat, Chothia, or combined Kabat and Chothia. In embodiments, the antibody molecule comprises a LC CDR1, LC CDR2, and LC CDR3 from SEQ ID NO: 10, wherein the CDRs are defined according to Kabat, Chothia, or combined Kabat and Chothia.

As used herein, "antibody molecule" refers to a protein, e.g., an immunoglobulin chain or fragment thereof, comprising at least one immunoglobulin variable domain sequence. The term "antibody molecule" encompasses antibodies and antibody fragments. In an embodiment, an antibody molecule is a multispecific antibody molecule, e.g., a bispecific antibody molecule.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005).

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273,927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

Pharmaceutical Compositions

Any of the peptides, fusion proteins, or other therapeutics described herein can be incorporated into pharmaceutical compositions. Such compositions may include one or more of the peptides (and/or nucleic acids encoding the peptides) and a pharmaceutically acceptable carrier. The composition may further include pembrolizumab. As used herein the language "pharmaceutically acceptable carrier" includes solvents, dispersion media, coatings, antibacterial and antifungal agents, isotonic and absorption delaying agents, and the like, compatible with pharmaceutical administration. One or more peptides can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds (e.g., one or more chemotherapeutic agents) can also be incorporated into the compositions. In embodiments, the composition comprises two or more (e.g., 2, 3, 4, 5, or 6) of the peptides described herein. The composition may also include an immunogenic peptide other than one disclosed herein, e.g., a peptide from WT1 or a derivative thereof, e.g., as described herein. Other immunogenic peptides include, but are not limited to, an immunogenic peptide from MUC1, an immunogenic peptide from gp100, an immunogenic peptide from TRP-2, an immunogenic peptide from MAGI, an immunogenic peptide from NY-ESO1, an immunogenic peptide from HER-2; and an immunogenic peptide from AIM2.

A pharmaceutical composition is generally formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic. Additional formulations, e.g., for the peptide compositions, are described in International Application WO2014/071402, which is herein incorporated by reference in its entirety, including the section therein on pages 77-81 entitled "Pharmaceutical Compositions".

In embodiments, the one or more peptides are formulated for injection, e.g., subcutaneous injection. In embodiments, the pembrolizumab is formulated for injection, e.g., intravenous injection.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the peptides (or fusion proteins or nucleic acids) can be formulated into ointments, salves, gels, or creams as generally known in the art.

In one embodiment, the compositions herein (e.g., peptides and/or antibody molecules) can be prepared with carriers that will protect the peptide or antibody molecule against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to, e.g., APCs with monoclonal antibodies to APC-specific antigens) can also be used as pharmaceutically acceptable carriers. These can be prepared according to methods known to those skilled in the art, for example, as described in U.S. Pat. No. 4,522,811.

Any of the pharmaceutical compositions described herein can be included in a container, pack, or dispenser together with instructions for administration as described below.

Applications

The combination therapies, compositions, pharmaceutical compositions, and kits herein can be used in a variety of methods. For example, the combination therapies and compositions described herein can be used to: (i) induce an immune response in a subject with a solid tumor, e.g., a breast cancer; (ii) activate a T cell in culture (e.g., a central memory T cell and/or effector memory T cell); and/or (iii) treat or even prevent a solid tumor, e.g., a breast cancer. Solid tumors include, e.g., lung cancer, liver cancer, bile duct cancer, stomach cancer, cervical cancer, nasopharyngeal cancer, breast cancer, colon cancer, pancreatic cancer, and prostate cancer. In some embodiments, the cancer, e.g., the breast cancer, is relapsed or refractory. In some embodiments, the cancer is relapsed or refractory triple negative breast cancer.

While the utility of the combination therapies, compositions, pharmaceutical compositions, and kits herein is in no way limited to any of the particular embodiments described herein, exemplary methods in which these reagents can be used are provided below.

Methods for Inducing an Immune Response

The disclosure also features a variety of methods for inducing an immune response in a subject having a cancer, e.g., a breast cancer. The methods for inducing an immune response in a subject having a cancer can include the step of administering to a subject one or more of any of combinations described herein or any of the pharmaceutical compositions described herein. The immune response can be a $CD8^+$ T cell, a $CD4^+$ T cell, a cytotoxic T lymphocyte (CTL), a $T_H1$ response, a $T_H2$ response, or a combination of both types of responses.

The combination therapies herein can be used in a variety of applications such as methods for inducing an immune response in a subject, methods for producing an antibody in a subject, and methods for treating a cancer, e.g., a breast cancer, e.g., triple negative breast cancer.

Any of the methods herein can also be, e.g., methods for treating or preventing (prophylaxis against) a cancer (e.g., breast cancer, e.g., triple negative breast cancer, or any other cancer expressing XBP1, CD138, or CS1) in a subject. When the terms "prevent," "preventing," or "prevention" are used herein in connection with a given treatment for a given condition, they mean that the treated subject does not develop a clinically observable level of the condition at all (e.g., the subject does not exhibit one or more symptoms of the condition or, in embodiments, the subject does not develop a detectable level of the cancer).

As used herein, the term "treat" "treatment," or "treating" a subject having a disorder, e.g., a cancer, are used in connection with a given treatment for a given disorder, wherein at least one symptom of the disorder is cured, healed, alleviated, relieved, altered, remedied, ameliorated, or improved. Treating includes administering an amount of a composition effective to alleviate, relieve, alter, remedy, ameliorate, improve or affect the disorder or the symptoms of the disorder. The treatment may inhibit deterioration or worsening of a symptom of a disorder or may cause the condition to develop more slowly and/or to a lesser degree (e.g., fewer symptoms or lower numbers of cancer cells in the subject) in the subject than it would have absent the treatment. For example, a treatment will be said to have "treated" the condition if it is given during the condition, e.g., during an early diagnosis of a cancer (e.g., the detection of a few cancer cells in a sample from the subject) that would have been expected to produce a given manifestation of the condition (an advanced cancer), and results in the subject's experiencing fewer and/or milder symptoms of the condition than otherwise expected. A treatment can "treat" a cancer (e.g., breast cancer, e.g., triple negative breast cancer) when the subject displays only mild overt symptoms of the cancer.

In an embodiment, the cancer is a cancer described herein. For example, the cancer can be a cancer of the bladder (including accelerated and metastatic bladder cancer), breast (e.g., estrogen receptor positive breast cancer, estrogen receptor negative breast cancer, HER-2 positive breast cancer, HER-2 negative breast cancer, triple negative breast cancer, inflammatory breast cancer), colon (including colorectal cancer), kidney (e.g., renal cell carcinoma (e.g., papillary renal cell carcinoma, clear cell carcinoma, chromphobic carcinoma)), liver, lung (including small cell lung cancer and non-small cell lung cancer (including adenocarcinoma, squamous cell carcinoma, bronchoalveolar carcinoma and large cell carcinoma)), genitourinary tract, e.g., ovary (including fallopian, endometrial and peritoneal cancers), cervix, prostate and testes, lymphatic system, rectum, larynx, pancreas (including exocrine pancreatic carcinoma), stomach (e.g., gastroesophageal, upper gastric or lower gastric cancer), gastrointestinal cancer (e.g., anal cancer or bile duct cancer), gall bladder, thyroid, leukemia (e.g., acute myeloid leukemia), neural and glial cell cancers (e.g., glioblastoma multiforme), and head and neck (e.g., nasopharyngeal cancer).

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted reagent production cells). See, e.g., U.S. Pat. Nos. 4,407,957, 5,798,113 and 5,800,828, each incorporated herein by reference in their entirety.

In general, the dosage of a peptide or an antibody molecule required depends on the choice of the route of administration; the nature of the formulation; the nature or severity of the subject's illness; the immune status of the subject; the subject's size, weight, surface area, age, and sex; other drugs being administered; and the judgment of the attending medical professional.

Suitable dosages of peptide for inducing an immune response are in the range of 0.000001 to 10 mg of the reagent or antigenic/immunogenic composition per kg of the subject. Variations in the needed dosage are to be expected in view of the variety of reagents and the differing efficiencies of various routes of administration. For example, nasal or rectal administration may require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). For example, a peptide or peptides can be administered as an initial immunization and then administered one or more times subsequently as a booster immunization.

In order to optimize therapeutic efficacy (e.g., the efficacy of the one or more peptides or the nucleic acids encoding the peptides to induce an immune response in a subject), compositions containing the peptides can be first administered at different dosing regimens. The unit dose and regimen depend on factors that include, e.g., the species of mammal, its immune status, the body weight of the mammal.

The frequency of dosing for a pharmaceutical composition (e.g., a pharmaceutical composition described herein) is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status.

In some embodiments, a pharmaceutical composition can be administered to a subject at least two (e.g., three, four, five, six, seven, eight, nine, 10, 11, 12, 15, or 20 or more) times. For example, a pharmaceutical composition can be administered to a subject once a month for three months; once a week for a month; every other week, once a year for three years, once a year for five years; once every five years; once every ten years; or once every three years for a lifetime.

In some embodiments, the reagent can be administered with an immune modulator such as a Toll Receptor ligand or an adjuvant (see below).

As defined herein, a "therapeutically effective amount" of a peptide or a nucleic acid encoding a peptide is an amount of the peptide or nucleic acid that is capable of producing an immune response in a treated subject. A therapeutically effective amount of a peptide (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A therapeutically effective amount of a nucleic acid also includes microgram, nanogram, or picogram amounts of the reagent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

As defined herein, a "prophylactically effective amount" of a peptide or nucleic acid encoding a peptide is an amount of the peptide or nucleic acid that is capable of producing an immune response against a cancer cell (e.g., a breast cancer cell) in a treated subject, which immune response is capable of preventing the development of a cancer in a subject or is able to substantially reduce the chance of a subject developing or continue developing a cancer (see above). A prophylactically effective amount of a peptide (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram). A prophylactically effective amount of a nucleic acid also includes microgram, nanogram, or picogram amounts of the reagent per kilogram of subject or sample weight (e.g., about 1 nanogram per kilogram to about 500 micrograms per kilogram, about 1 microgram per kilogram to about 500 micrograms per kilogram, about 100 micrograms per kilogram to about 500 micrograms per kilogram, or about 1 microgram per kilogram to about 50 micrograms per kilogram).

The subject can be any animal capable of an immune response to an antigen such as, but not limited to, a mammal, e.g., a human (e.g., a human patient) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. The subject can be one having, suspected of having, or at risk of developing a solid tumor such as breast cancer e.g., triple negative breast cancer, or any other type of solid tumor that expresses XBP1, CD138, or CS-1 (e.g., lung cancer, liver cancer, bile duct cancer, stomach cancer, cervical cancer, nasopharyngeal cancer, colon cancer, or pancreatic cancer). The subject can be one in remission from the cancer, e.g., the breast cancer.

The methods can also include the step of, prior to administering the one or more peptides (or nucleic acids) to the subject, determining whether one or more cancer cells of the subject's cancer (e.g., breast cancer) express XBP1, CD138, or CS-1. Expression of these proteins includes both mRNA and protein expression. Methods for detecting protein and mRNA expression in a cell include, e.g., enzyme-linked immunosorbent assay (ELISA), western and dot-blotting techniques, or immunohistochemistry techniques for detecting protein and reverse transcription-polymerase chain reaction (RT-PCR) or northern-blotting techniques for detecting mRNA.

The peptides or composition may be used in combination with other known therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, delivery is such that the combination therapy results in a greater immune response observed than in a patient treated only with the same dose of the one or more peptides. In some embodiments, delivery is such that the combination therapy results in a greater clinical response observed than in a patient treated only with the same dose of the one or more peptides. In some embodiments, delivery is such that the combination therapy results in a greater clinical response observed than in a patient treated only with the same dose of the pembrolizumab. In some embodiments, delivery is such that the combination therapy results in a similar clinical response between the combination therapy and a pembrolizumab monotherapy, wherein the pembrolizumab is administered less frequently or at a lower dose as part of the combination therapy than as a monotherapy.

In some embodiments, the method of treatment comprises administering: (a) one or more peptides described herein, (b) pembrolizumab, and (c) one or more additional treatment. In embodiments, the additional treatment comprises surgery, chemotherapy (e.g., adjuvant or neo-adjuvant chemotherapy).

The additional treatment can be, e.g., surgery, one or more chemotherapeutic agents, one or more forms of ionizing radiation, and/or one or more immunomodulatory agents.

The one or more forms of ionizing radiation can be gamma-irradiation, X-irradiation, or beta-irradiation.

Exemplary classes of chemotherapeutic agents include, e.g., the following:

alkylating agents (including, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®).

anti-EGFR antibodies (e.g., cetuximab (Erbitux®) and panitumumab (Vectibix®).

anti-HER-2 antibodies (e.g., trastuzumab (Herceptin®).

antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®) and gemcitabine (Gemzar®). Suitable antimetabolites include, e.g., 5-fluorouracil (Adrucil®, Efudex®, Fluoroplex®), floxuridine (FUDF®), capecitabine (Xeloda®), pemetrexed (Alimta®), raltitrexed (Tomudex®) and gemcitabine (Gemzar®).

vinca alkaloids: vinblastine (Velban®, Velsar®), vincristine (Vincasar®, Oncovin®), vindesine (Eldisine®), vinorelbine (Navelbine®).

platinum-based agents: carboplatin (Paraplat®, Paraplatin®), cisplatin (Platinol®), oxaliplatin (Eloxatin®).

anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®).

topoisomerase inhibitors: topotecan (Hycamtin®), irinotecan (Camptosar®), etoposide (Toposar®, VePesid®), teniposide (Vumon®), lamellarin D, SN-38, camptothecin.

taxanes: paclitaxel (Taxol®), docetaxel (Taxotere®), larotaxel, cabazitaxel.

epothilones: ixabepilone, epothilone B, epothilone D, BMS310705, dehydelone, ZK-Epothilone (ZK-EPO).

poly ADP-ribose polymerase (PARP) inhibitors: (e.g., BSI 201, Olaparib (AZD-2281), ABT-888, AG014699, CEP 9722, MK 4827, KU-0059436 (AZD2281), LT-673, 3-aminobenzamide).

antibiotics: actinomycin (Cosmegen®), bleomycin (Blenoxane®), hydroxyurea (Droxia®, Hydrea®), mitomycin (Mitozytrex®, Mutamycin®).

immunomodulators: lenalidomide (Revlimid®), thalidomide (Thalomid®).

immune cell antibodies: alemtuzamab (Campath®), gemtuzamab (Myelotarg®), rituximab (Rituxan®), tositumomab (Bexxar®).

interferons (e.g., IFN-alpha (Alferon®, Roferon-A®, Intron®-A) or IFN-gamma (Actimmune®)).

interleukins: IL-1, IL-2 (Proleukin®), IL-24, IL-6 (Sigosix®), IL-12.

HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG").

angiogenesis inhibitors which include, without limitation A6 (Angstrom Pharmacueticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP 02) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharaceuticals), Combretastatin (Oxigene), CP-751,871 (Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518 (Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

anti-androgens which include, without limitation nilutamide (Nilandron®) and bicalutamide (Caxodex®).

antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride.

anti-hypercalcaemia agents which include without limitation gallium (III) nitrate hydrate (Ganite®) and pamidronate disodium (Aredia®).

apoptosis inducers which include without limitation ethanol, 2-[[3-(2,3-dichlorophenoxy)propyl]amino]-(9Cl), gambogic acid, embelin and arsenic trioxide (Trisenox®).

Aurora kinase inhibitors which include without limitation binucleine 2.

Bruton's tyrosine kinase inhibitors which include without limitation terreic acid.

calcineurin inhibitors which include without limitation cypermethrin, deltamethrin, fenvalerate and tyrphostin 8.

CaM kinase II inhibitors which include without limitation 5-Isoquinolinesulfonic acid, 4-[(2S)-2-[(5-isoquinolinylsulfonyl)methylamino]-3-oxo-3-14-phenyl-1-piperazinyl)propyl]phenyl ester and benzenesulfonamide.

CD45 tyrosine phosphatase inhibitors which include without limitation phosphonic acid.

CDC25 phosphatase inhibitors which include without limitation 1,4-naphthalene dione, 2,3-bis[(2-hydroxyethyl) thio]-(9Cl).

CHK kinase inhibitors which include without limitation debromohymenialdisine.

cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid).

cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl).

cyclin dependent kinase inhibitors which include without limitation olomoucine and its derivatives, purvalanol B, roascovitine (Seliciclib®), indirubin, kenpaullone, purvalanol A and indirubin-3'-monooxime.

cysteine protease inhibitors which include without limitation 4-morpholinecarboxamide, N-[(1S)-3-fluoro-2-oxo-1-(2-phenylethyl)propyl]amino]-2-oxo-1-(phenylmethyl) ethyl]-(9Cl).

DNA intercalators which include without limitation plicamycin (Mithracin®) and daptomycin (Cubicin®).

DNA strand breakers which include without limitation bleomycin (Blenoxane®).

E3 ligase inhibitors which include without limitation N-((3,3,3-trifluoro-2-trifluoromethyl)propionyl) sulfanilamide.

EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980.

farnesyltransferase inhibitors which include without limitation A-hydroxyfarnesylphosphonic acid, butanoic acid, 2-[(2S)-2-[[(2S,3S)-2-[[(2R)-2-amino-3-mercaptopropyl] amino]-3-methylpentyl]oxy]-1-oxo-3-phenylpropyl] amino]-4-(methylsulfonyl)-1-methylethylester (2S)-(9Cl), and manumycin A.

Flk-1 kinase inhibitors which include without limitation 2-propenamide, 2-cyano-3-[4-hydroxy-3,5-bis(1-methylethyl)phenyl]-N-(3-phenylpropyl)-(2E)-(9Cl).

glycogen synthase kinase-3 (GSK3) inhibitors which include without limitation indirubin-3'-monooxime.

Heat Shock Protein 90 (Hsp90) chaperone modulators which include without limitation AUY922, STA-9090, ATI13387, MCP-3100, IPI-504, IPI-493, SNX-5422, Debio0932, HSP990, DS-2248, PU-H71, 17-DMAG (Alvespimycin), and XL888.

histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin and compounds disclosed in WO 02/22577.

I-kappa B-alpha kinase inhibitors (IKK) which include without limitation 2-propenenitrile, 3-[(4-methylphenyl) sulfonyl]-(2E)-(9Cl).

imidazotetrazinones which include without limitation temozolomide (Methazolastone®, Temodar® and its derivatives (e.g., as disclosed generically and specifically in U.S. Pat. No. 5,260,291) and Mitozolomide.

Insulin like growth factor pathway inhibitors such as IGF inhibitors or IGF receptor (IGFR1 or IGFR2) inhibitors include without limitation, small molecule inhibitors, e.g., OSI-906; anti-IGF antibodies or anti-IGFR antibodies, e.g., AVE-1642, MK-0646, IMC-A12 (cixutumab), R1507, CP-751,871 (Figitumumab).

insulin tyrosine kinase inhibitors which include without limitation hydroxyl-2-naphthalenylmethylphosphonic acid.

c-Jun-N-terminal kinase (JNK) inhibitors which include without limitation pyrazoleanthrone and epigallocatechin gallate.

mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hydroxyethyl)-4-methoxy-(9Cl).

MDM2 inhibitors which include without limitation trans-4-iodo, 4'-boranyl-chalcone.

MEK inhibitors which include without limitation butanedinitrile, bis[amino[2-aminophenyl)thio]methylene]-(9Cl).

MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996.

mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD.

NGFR tyrosine kinase inhibitors which include without limitation tyrphostin AG 879.

p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl).

p56 tyrosine kinase inhibitors which include without limitation damnacanthal and tyrphostin 46.

PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854.

phosphatidylinositol 3-kinase inhibitors which include without limitation wortmannin, and quercetin dihydrate.

phosphatase inhibitors which include without limitation cantharidic acid, cantharidin, and L-leucinamide.

PKC inhibitors which include without limitation 1-H-pyrollo-2,5-dione,3-[1-[3-(dimethylamino)propyl]-1H-indol-3-yl]-4-(1H-indol-3-yl)-(9Cl), Bisindolylmaleimide IX, Sphinogosine, staurosporine, and Hypericin.

PKC delta kinase inhibitors which include without limitation, rottlerin.

polyamine synthesis inhibitors which include without limitation, DMFO.

proteasome inhibitors which include, without limitation, aclacinomycin A, gliotoxin and bortezomib (Velcade®).

protein phosphatase inhibitors which include without limitation cantharidic acid, cantharidin, L-P-bromotetramisole oxalate, 2 (5H)-furanone, 4-hydroxy-5-(hydroxymethyl)-3-(1-oxohexadecyl)-(5R)-(9Cl) and benzylphosphonic acid.

protein tyrosine kinase inhibitors which include, without limitation tyrphostin Ag 216, tyrphostin Ag 1288, tyrphostin Ag 1295, geldanamycin, genistein and 7H-pyrollo[2,3-d]pyrimidine derivatives;

PTP1B inhibitors which include without limitation L-leucinamide.

SRC family tyrosine kinase inhibitors which include without limitation PP1 and PP2.

Syk tyrosine kinase inhibitors which include without limitation piceatannol.

Janus (JAK-2 and/or JAK-3) tyrosine kinase inhibitors which include without limitation tyrphostin AG 490 and 2-naphthyl vinyl ketone.

retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®).

RNA polymerase II elongation inhibitors which include without limitation 5,6-dichloro-1-beta-D-ribofuranosylbenzimidazole.

serine/threonine kinase inhibitors which include without limitation 2-aminopurine.

sterol biosynthesis inhibitors which include without limitation squalene epoxidase and CYP2D6.

VEGF pathway inhibitors which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632, AV-951 (tivozanib) and AZD2171 (also known as cediranib) (Recentin™).

For example, one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, thalidomide, lenalidomide, a proteosome inhibitor (e.g., bortezomib), an hsp90 inhibitor (e.g., tenespinmycin), transplatinum, 5-flurouracil, vincristin, vinblastin, methotrexate, or an analog of any of the aforementioned. Immunomodulatory agents include, e.g., a variety of chemokines and cytokines such as Interleukin 2 (IL-2), granulocyte/macrophage-colony stimulating factor (GM-CSF), and Interleukin 12 (IL-12).

In one embodiment, the additional therapy is one or more additional immunogenic peptide, e.g., one or more immunogenic peptide from WT1 or a derivative thereof. Exemplary WT1 immunogenic peptides include, but are not limited to, a WT1 class 1 epitope; a peptide comprising (or consisting of) RMFPNAPYL (WT1 126-134); a peptide comprising (or consisting of) YMFPNAPYL; a peptide comprising (or consisting of) RSDELVRHHNMHQRNMTKL (WT1 427-445); a peptide comprising (or consisting of) PGCNK-RYFKLSHLQMHSRKHTG (WT1 331-352); a peptide comprising (or consisting of) SGQARMFPNAPYLPSCLES (WT1 122-140); and a peptide comprising (or consisting of) SGQAYMFPNAPYLPSCLES. Other WT1 immunogenic peptides are described in U.S. Pat. No. 7,598,221, the contents of which is incorporated herein by reference. Other immunogenic peptides include, but are not limited to, an immunogenic peptide from MUC1, an immunogenic peptide from gp100, an immunogenic peptide from TRP-2, an immunogenic peptide from MAGI, an immunogenic peptide from NY-ESO1, an immunogenic peptide from HER-2; and an immunogenic peptide from AIM2.

The subject can have, be suspected of having, or be at risk of developing a cancer such as breast cancer, e.g., triple negative breast cancer, e.g., metastatic triple negative breast cancer. A subject "suspected of having a cancer" is one having one or more symptoms of a cancer or having one or more lab test result, e.g., blood test result, suggestive of cancer. Symptoms of cancer are well-known to those of skill in the art and generally include, without limitation, pain, weight loss, weakness, excessive fatigue, difficulty eating, loss of appetite, chronic cough, worsening breathlessness, coughing up blood, blood in the urine, blood in stool, nausea, vomiting, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, difficulty swallowing, and the like.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC), has been exposed to conditions, or is presently affected by conditions, that can result in cancer. Thus, a subject can also be one "at risk of developing a cancer" when the subject has been exposed to mutagenic or carcinogenic levels of certain compounds (e.g., carcinogenic compounds in cigarette smoke such as acrolein, 4-aminobiphenyl, aromatic amines, benzene, benz{a}anthracene, benzo{a}pyrene, formaldehyde, hydrazine, Polonium-210 (Radon), urethane, or vinyl chloride). The subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. In addition, a subject can be "at risk of developing a cancer" when the subject suffers from an inflammation (e.g., chronic inflammation).

Triple negative breast cancer refers to a breast cancer that is negative for estrogen receptor (ER), progesterone receptor (PR), and HER2. Presence or absence of ER, PR, and HER2 can be assessed, e.g., by immunohistochemistry or quantitative PCR on a biopsy sample. This type of cancer is often treated with a combination of surgery and chemotherapy.

In some embodiments, the patient is human leukocyte antigen (HLA)-A2 positive.

In some embodiments, the patient has an Eastern Cooperative Oncology Group (ECOG) performance status of 0 or 1; has adequate bone marrow function, evidenced by a platelet count $\geq 75 \times 10^9/L$ and an absolute neutrophil count $(ANC) \geq 1.0 \times 10^9/L$; and/or has adequate hepatic function, evidenced by a bilirubin $\leq 2.0$ mg/dL and an alanine transaminase (ALT), and aspartate transaminase (AST) $\leq 2.5 \times$ the upper limit of normal (ULN).

In embodiments, (i) pembrolizumab and (ii) the one or more peptides are administered in an amount sufficient to increase progression free survival (PFS) relative to the expected course of disease without treatment, or compared to the expected course of disease upon treatment with (i) only or with (ii) only, or compared to the expected course of disease with standard of care treatment. In embodiments, (i) and (ii) are administered in an amount sufficient to increase overall survival (OS) relative to the expected course of disease without treatment, or compared to the expected course of disease upon treatment with (i) only or with (ii) only, or compared to the expected course of disease with standard of care treatment. In embodiments, (i) pembrolizumab and (ii) the one or more peptides are administered in an amount sufficient to give as good a clinical response (e.g., measured by PFS or OS) as a monotherapy with pembrolizumab, e.g., as good a clinical response with fewer adverse effects. PFS and OS can be determined according to the Response Evaluation Criteria in Solid Tumors (RECIST) guideline (version 1.1). In embodiments, (i) and (ii) are administered in an amount sufficient to induce an immune response to one or more of the peptides administered, e.g., a greater immune response than would have been observed without treatment or upon treatment with (i) only or (ii) only, or compared to the expected course of disease with standard of care treatment. Immune response can be measured, e.g., by an ELISPOT assay or as described in International Application WO2014/071402, which application is herein incorporated by reference in its entirety.

In some embodiments, the method can also include determining if an immune response occurred in a subject after administering a combination therapy described herein to the subject. Suitable methods for determining whether an immune response occurred in a subject include use of immunoassays to detect, e.g., the presence of antibodies specific for a peptide in a biological sample from the subject. For example, after the administration of the peptide or composition to the subject, a biological sample (e.g., a blood sample) can be obtained from the subject and tested for the presence of antibodies specific for the peptide(s). An immune response can also be detected by assaying for the presence or amount of activated T cells in a sample. Such assays include, e.g., proliferation assays, limiting dilution assays, cytotoxicity assays (e.g., lymphokine or $^{51}$Cr-release assays), or flow cytometry assays.

In some embodiments, the methods can also include the step of determining whether a subject has a cancer. Suitable methods for such a determination depend on the type of cancer to be detected in the subject, but are known in the art. Such methods can be qualitative or quantitative. Methods for diagnosing breast cancer include mammogram, ultrasounds, MRI, biopsy, and molecular tests. Methods for diagnosing triple negative breast cancer include immunohistochemistry for PR, ER, and HER2.

Methods for Selecting a Therapy

Methods for selecting a therapy for a subject with a cancer, e.g., a breast cancer or any cancer in which XBP1, CD138, or CS1 are expressed include the steps of: optionally, determining whether one or more cells (e.g., breast cancer cells) of a subject's cancer express XBP1; and if one or more cells express XBP1, selecting as a therapy for the subject: (i) pembrolizumab, and (ii) a peptide or composition described herein e.g., a XBP1 peptide or composition comprising a XBP1 peptide described herein.

Methods for selecting a therapy for a subject with a cancer, e.g., a breast cancer can include the steps of: optionally, determining whether one or more cells (e.g., breast cancer cells) of a subject's cancer express CD138; and if one or more cells express CD138, selecting as a therapy for the subject: (i) pembrolizumab, and (ii) a peptide or composition described herein e.g., a CD138 peptide or composition comprising a CD138 peptide described herein.

Methods for selecting a therapy for a subject with a cancer, e.g., a breast cancer can include the steps of: optionally, determining whether one or more cells (e.g., breast cancer cells) of a subject's cancer express CS-1; and if one or more cells express CS-1, selecting as a therapy for the subject: (i) pembrolizumab, and (ii) a peptide or composition described herein, e.g., a CS-1 peptide or composition comprising a CS-1 peptide described herein.

It is understood that where one or more cells (e.g., breast cancer cells) of a subject's cancer express two or more of XBP1, CD138, and CS-1, a combination of suitable peptides can be delivered to the subject, e.g., via a composition described herein, in further combination with pembrolizumab. Methods for determining whether one or more cells express XBP1, CD138, or CS-1 are described, e.g., in the section on p. 104-107 entitled "Methods for Selecting a Therapy" of International Application WO2014/071402, which application is herein incorporated by reference in its entirety.

Kits and Articles of Manufacture

The disclosure also features a variety of kits. The kits can include, e.g., (i) pembrolizumab, (ii) one or more (e.g., one, two, three, four, five, six, seven, eight, nine, or 10 or more) of any of the peptides or compositions (or expression vectors containing nucleic acid sequences encoding one or more peptides) described herein, and (iii) instructions for administering the peptide or composition to a subject. In embodiments, (ii) comprises one or more of, e.g., all of, (a) a non-spliced XBP1 peptide that is 35 amino acids or less in length and comprises the amino acid sequence of SEQ ID NO:1, (b) a spliced XBP1 peptide that is 35 amino acids or less in length and comprises the amino acid sequence of SEQ ID NO:2, or (c) a CD138 peptide that is 35 amino acids or less in length and comprises the amino acid sequence of SEQ ID NO:3. In embodiments (ii) comprises one or more of, e.g., all of, (a) a non-spliced XBP1 peptide that consists of the amino acid sequence of SEQ ID NO:1, (b) a spliced XBP1 peptide that consists of the amino acid sequence of SEQ ID NO:2, or (c) a CD138 peptide that consists of the amino acid sequence of SEQ ID NO:3. The kit can include one or more pharmaceutically acceptable carriers and/or one or more immune stimulating agents and/or one or more immune modulating agents. The immune stimulating agents can be, e.g., a T helper epitope, an altered peptide ligand, or an adjuvant. In one embodiment, the immune stimulating agent can be a combination of carboxymethylcellulose, polyinosinic-polycytidylic acid, and poly-L-lysine double-stranded RNA (e.g., poly IC-LC, e.g., hiltonol); a water-and-oil emulsion (e.g., montanide); or a protein (e.g., a cytokine, a complement, GCSF, or GM-CSF). In one embodiment, the additional agent can be a protein, e.g., an antibody. In one embodiment, the additional agent is an immune checkpoint inhibitor. For example, an antibody which inhibits an immune checkpoint molecule can be an anti-CTLA4 antibody, e.g., ipilimumab or tremelimumab, or an anti-PD-1 antibody, or anti-PDL-1 antibody. In one embodiment, the additional agent can be a small molecule adjuvant, e.g., thalidomide or a thalidomide derivative, e.g., lenalidomide.

The kits can also contain one or more therapeutic agents, diagnostic agents, or prophylactic agents. The one or more therapeutic, diagnostic, or prophylactic agents include, but are not limited to: (i) an agent that modulates inflammatory responses (e.g., aspirin, indomethacin, ibuprofen, naproxen, steroids, cromolyn sodium, or theophylline); (ii) an agent that affects renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, or mevalonate); (iii) drugs that affect gastrointestinal function (e.g., omeprazole or sucralfate); (iv) antibiotics (e.g., tetracycline, clindamycin, amphotericin B, quinine, methicillin, vancomycin, penicillin G, amoxicillin, gentamicin, erythromycin, ciprofloxacin, doxycycline, streptomycin, gentamicin, tobramycin, chloramphenicol, isoniazid, fluconazole, or amantadine); (v) anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, or decarbazine); (vi) immunomodulatory agents (e.g., interleukins, interferons (e.g., interferon gamma (IFN-γ), granulocyte macrophage-colony stimulating factor (GM-CSF), tumor necrosis factor alpha (TNFα), tumor necrosis factor beta (TNFβ), cyclosporine, FK506, azathioprine, steroids); (ix) drugs acting on the blood and/or the blood-forming organs (e.g., interleukins, G-CSF, GM-CSF, erythropoietin, heparin, warfarin, or coumarin); or (vii) hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphosphonates, calcitonin, fluoride).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating breast cancer comprising administering to a subject:
 (i) pembrolizumab; and
 (ii) each of:
  (a) a non-spliced XBP1 peptide of 35 amino acids or less in length comprising SEQ ID NO: 1;
  (b) a spliced XBP1 peptide of 35 amino acids or less in length comprising SEQ ID NO: 2;
  (c) a CD138 peptide of 35 amino acids or less in length comprising SEQ ID NO: 3; and
  (d) a CS-1 peptide of 35 amino acids or less in length comprising SEQ ID NO: 4;
wherein the subject has, or is at risk of developing, breast cancer.

2. The method of claim 1, wherein:
 (i) the non-spliced XBP1 peptide consists of the amino acid sequence of SEQ ID NO:1;
 (ii) the spliced XBP1 peptide consists of the amino acid sequence of SEQ ID NO:2;
 (iii) the CD138 peptide consists of the amino acid sequence of SEQ ID NO:3; or
 (iv) the CS-1 peptide consists of the amino acid sequence of SEQ ID NO:4, or any combination thereof.

3. The method of claim 1, wherein the breast cancer is triple negative breast cancer.

4. The method of claim 1, wherein the breast cancer is metastatic breast cancer.

5. The method of claim 1, wherein the subject has, or is identified as having, one or more cancer cells that express XBP1, CD138, or CS1, or any combination thereof.

6. The method of claim 1, wherein the subject is a human.

7. The method of claim 1, wherein (i) and (ii) are administered separately or together.

8. The method of claim 1, wherein (i) is administered before, concurrently with, or after (ii).

9. The method of claim 1, wherein the pembrolizumab is administered at a dose of 200 mg.

10. The method of claim 1, wherein the pembrolizumab is administered every 3 weeks.

11. The method of claim 1, wherein the peptides are administered at a dose of about 0.6 mg total peptide.

12. The method of claim 1, wherein the peptides are administered once every week.

* * * * *